(12) United States Patent  (10) Patent No.: US 8,137,312 B2
Sundar et al. (45) Date of Patent: Mar. 20, 2012

(54) DETECTION APPARATUS AND METHOD

(75) Inventors: Satish Sundar, Milpitas, CA (US);
Swaminathan Balakrishnan, London (GB); Albert Hartman, Palo Alto, CA (US)

(73) Assignee: Indigo Orb, Inc., Irvine, CA (US)

( * ) Notice: Subject to any disclaimer, the term of this patent is extended or adjusted under 35 U.S.C. 154(b) by 1199 days.

(21) Appl. No.: 10/543,754

(22) PCT Filed: Jan. 28, 2004

(86) PCT No.: PCT/GB2004/000338
§ 371 (c)(1),
(2), (4) Date: May 21, 2007

(87) PCT Pub. No.: WO2004/066853

PCT Pub. Date: Aug. 12, 2004

(65) Prior Publication Data
US 2007/0142766 A1    Jun. 21, 2007

(30) Foreign Application Priority Data
Jan. 28, 2003   (GB) .................................. 0301934.6

(51) Int. Cl.
*A61M 1/00*   (2006.01)
(52) U.S. Cl. ...................................................... 604/121
(58) Field of Classification Search .................... 604/121
See application file for complete search history.

(56) References Cited

U.S. PATENT DOCUMENTS

| 1,527,291 | A | * | 2/1925 | Zorraquin ..................... 604/158 |
| 4,215,699 | A | | 8/1980 | Patel |
| 4,838,864 | A | * | 6/1989 | Peterson ................... 604/100.02 |
| 4,919,653 | A | | 4/1990 | Martinez et al. |
| 4,940,458 | A | | 7/1990 | Cohn |
| 4,944,724 | A | | 7/1990 | Goldberg et al. |
| 5,024,662 | A | | 6/1991 | Menes et al. |
| 5,188,594 | A | | 2/1993 | Zilberstein |
| 5,205,828 | A | | 4/1993 | Kedem et al. |
| 5,207,647 | A | | 5/1993 | Phelps |
| 5,258,003 | A | | 11/1993 | Ciaglia et al. |
| 5,356,386 | A | | 10/1994 | Goldberg et al. |
| 5,395,345 | A | | 3/1995 | Gross |
| 5,397,313 | A | | 3/1995 | Gross |
| 5,429,612 | A | | 7/1995 | Berthier |
| 5,470,318 | A | | 11/1995 | Griffith, III et al. |
| 5,472,430 | A | | 12/1995 | Vaillancourt et al. |

(Continued)

FOREIGN PATENT DOCUMENTS
CN    2254334 Y    5/1997
(Continued)

OTHER PUBLICATIONS

Final Office Action mailed on Nov. 15, 2010, for U.S. Appl. No. 11/706,801, filed Feb. 14, 2007, 7 pages.

(Continued)

*Primary Examiner* — Nicholas Lucchesi
*Assistant Examiner* — Jason Flick
(74) *Attorney, Agent, or Firm* — Morrison & Foerster LLP

(57) ABSTRACT

A detection apparatus for, and a method of, detecting the location of the tip of a tubular element, in particular a needle, within a region, in particular one of the epidural space and the peritoneal cavity.

44 Claims, 10 Drawing Sheets

U.S. PATENT DOCUMENTS

| | | | |
|---|---|---|---|
| 5,531,696 A | 7/1996 | Menes | |
| 5,549,573 A | 8/1996 | Waskönig | |
| 5,616,133 A | 4/1997 | Cardenas | |
| 5,722,955 A | 3/1998 | Racz | |
| 5,725,509 A | 3/1998 | Scarfone et al. | |
| 5,735,825 A | 4/1998 | Stevens et al. | |
| 5,738,650 A | 4/1998 | Gregg | |
| 5,836,914 A | 11/1998 | Houghton | |
| 5,871,470 A | 2/1999 | McWha | |
| 5,902,273 A | 5/1999 | Yang et al. | |
| 5,919,172 A | 7/1999 | Golba, Jr. | |
| 6,004,293 A | 12/1999 | Bell | |
| 6,010,493 A | 1/2000 | Snoke | |
| 6,086,559 A | 7/2000 | Enk et al. | |
| 6,135,153 A | 10/2000 | Cleland, Sr. et al. | |
| 6,171,286 B1 | 1/2001 | Gross | |
| 6,190,370 B1 | 2/2001 | Tsui | |
| 6,245,044 B1 | 6/2001 | Daw et al. | |
| 6,273,877 B1 | 8/2001 | West et al. | |
| 6,743,203 B1 | 6/2004 | Pickhard | |
| 6,773,417 B2 | 8/2004 | Fitzgibbons et al. | |
| 6,786,365 B2 | 9/2004 | Kim | |
| 6,830,564 B2 | 12/2004 | Gray | |
| 6,964,356 B2 | 11/2005 | Kim | |
| 7,002,098 B2 | 2/2006 | Adams | |
| 2002/0165490 A1 | 11/2002 | Minezaki et al. | |
| 2003/0009135 A1 | 1/2003 | Fitzgibbons et al. | |
| 2003/0168480 A1 | 9/2003 | Kim | |
| 2004/0087931 A1 | 5/2004 | Marsh et al. | |
| 2004/0186430 A1 | 9/2004 | Hasan et al. | |
| 2004/0215080 A1 | 10/2004 | Lechner | |
| 2005/0267420 A1 | 12/2005 | Young | |
| 2006/0015073 A9 | 1/2006 | Ferguson et al. | |
| 2006/0173418 A1 | 8/2006 | Rinaudo et al. | |
| 2006/0173480 A1 | 8/2006 | Zhang | |
| 2007/0213674 A1 | 9/2007 | Sundar et al. | |
| 2007/0232993 A1 | 10/2007 | Sundar et al. | |
| 2007/0244446 A1 | 10/2007 | Sundar et al. | |

FOREIGN PATENT DOCUMENTS

| | | |
|---|---|---|
| CN | 2293336 Y | 10/1998 |
| EP | 0 091 846 A1 | 10/1983 |
| EP | 0 538 259 A1 | 4/1993 |
| EP | 0 608 659 A1 | 8/1994 |
| GB | 2 316 320 A | 2/1998 |
| GB | 2 366 729 A | 3/2002 |
| WO | WO-93/08852 A1 | 5/1993 |
| WO | WO-99/04705 A1 | 2/1999 |
| WO | WO-01/07104 A1 | 2/2001 |
| WO | WO-01/91651 A1 | 12/2001 |
| WO | WO-03/000146 A1 | 1/2003 |

OTHER PUBLICATIONS

Non-Final Office Action mailed Apr. 26, 2010, for U.S. Appl. No. 11/706,801, filed Feb. 14, 2007, 6 pages.

Non-Final Office Action mailed on Jul. 7, 2010, for U.S. Appl. No. 11/706,552, filed Feb. 14, 2007, 6 pages.

Non-Final Office Action mailed on Jul. 8, 2010, for U.S. Appl. No. 11/706,780, filed Feb. 14, 2007, 7 pages.

International Search Report mailed Sep. 20, 2004 for PCT Application No. WO/GB2004/000338 filed on Jan. 28, 2004, 5 pages.

Final Office Action mailed on Feb. 17, 2011, for U.S. Appl. No. 11/706,552, filed Feb. 14, 2007, 7 pages.

Final Office Action mailed on Feb. 17, 2011, for U.S. Appl. No. 11/706,780, filed Feb. 14, 2007, 7 pages.

Non-Final Office Action mailed on Feb. 18, 2011, for U.S. Appl. No. 11/706,801, filed Feb. 14, 2007, 7 pages.

Final Office Action mailed on Aug. 4, 2011, for U.S. Appl. No. 11/706,801, filed Feb. 14, 2007, 8 pages.

* cited by examiner

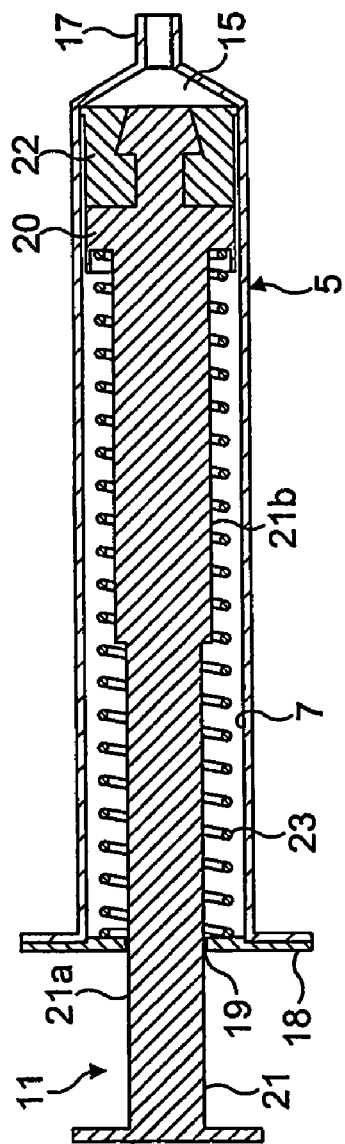
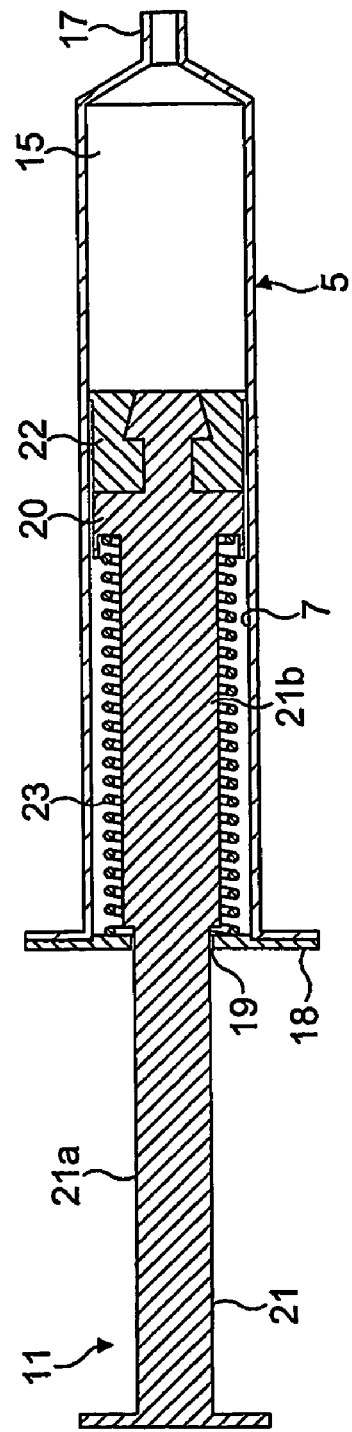
FIG. 1(a)
FIG. 1(b)

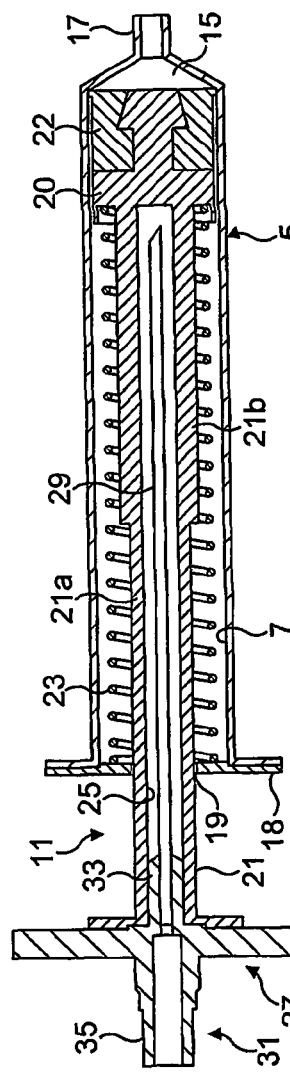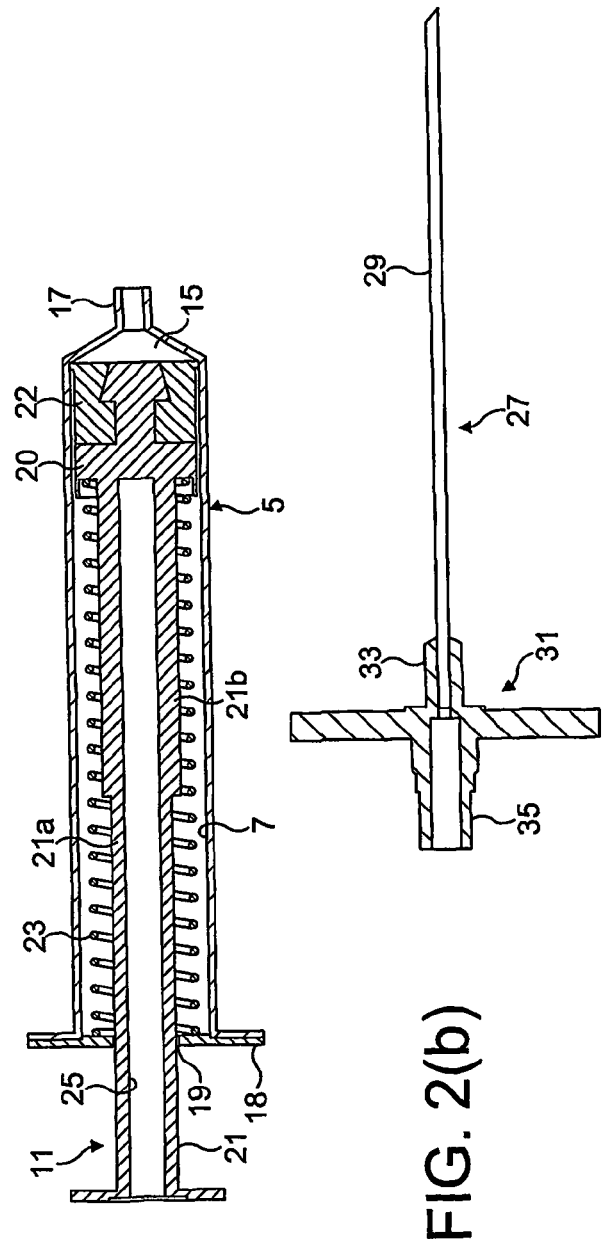
FIG. 2(a)
FIG. 2(b)

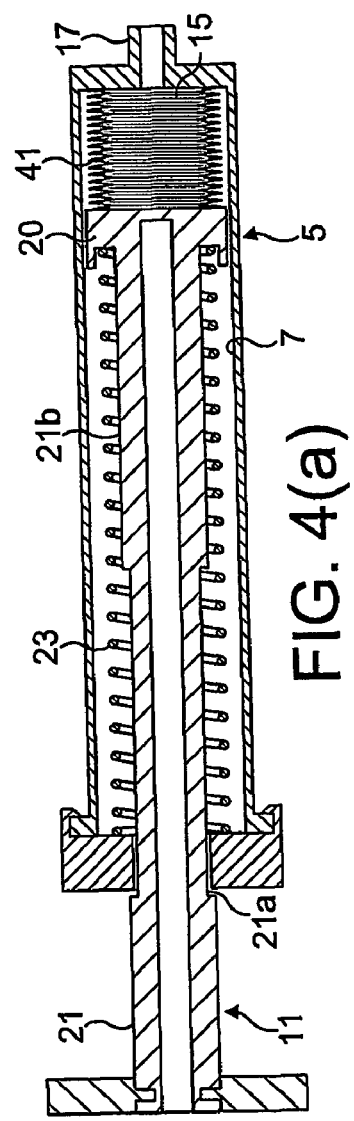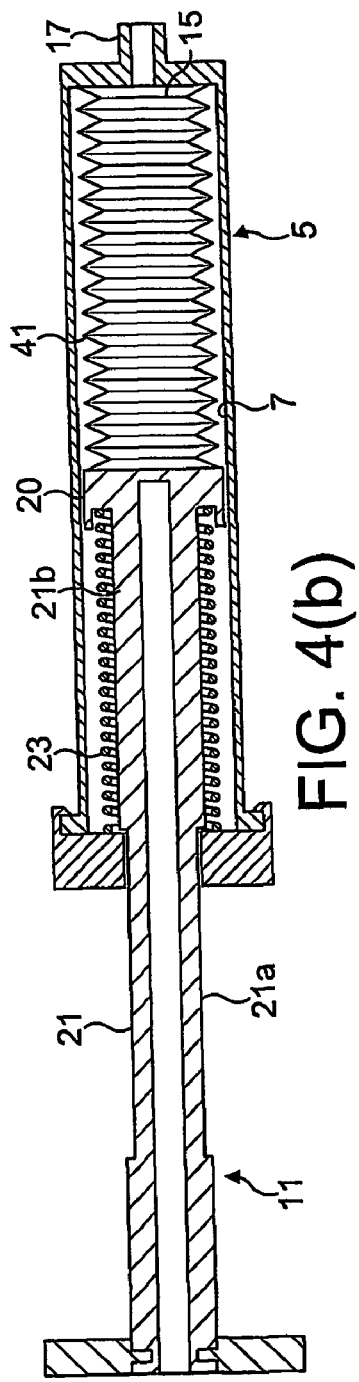
FIG. 4(a)
FIG. 4(b)

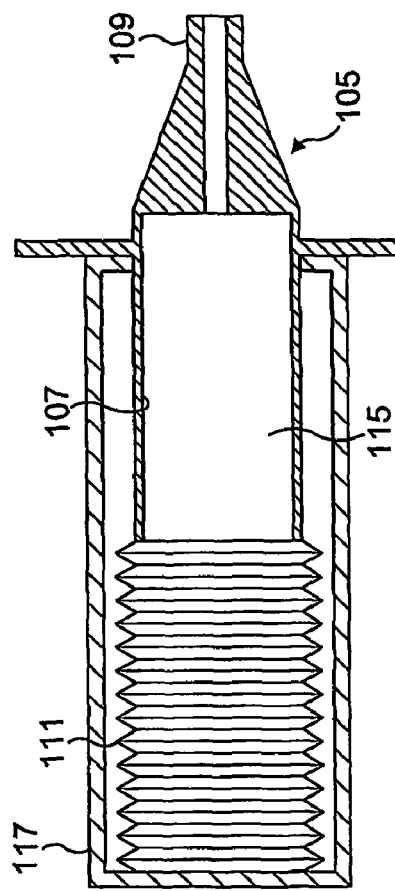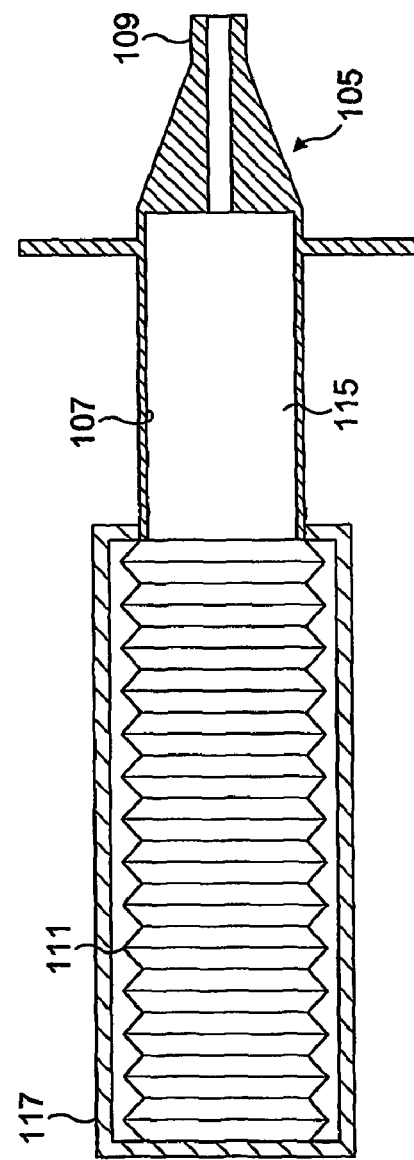

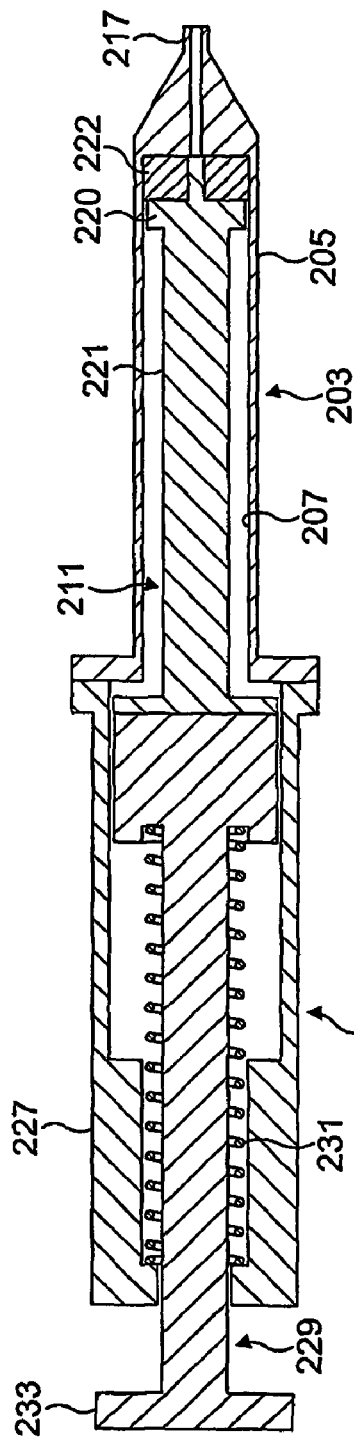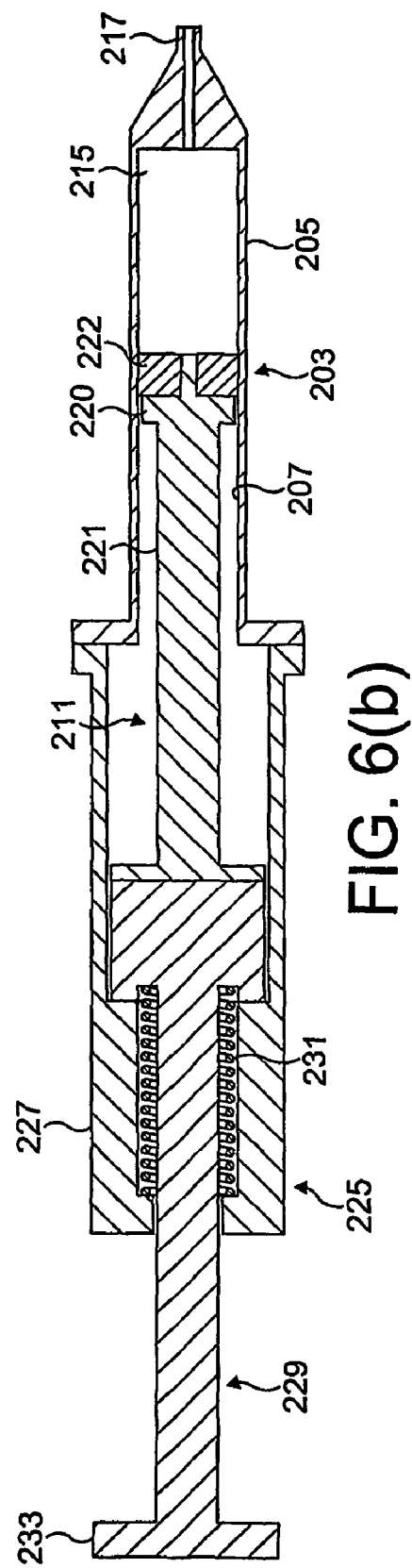

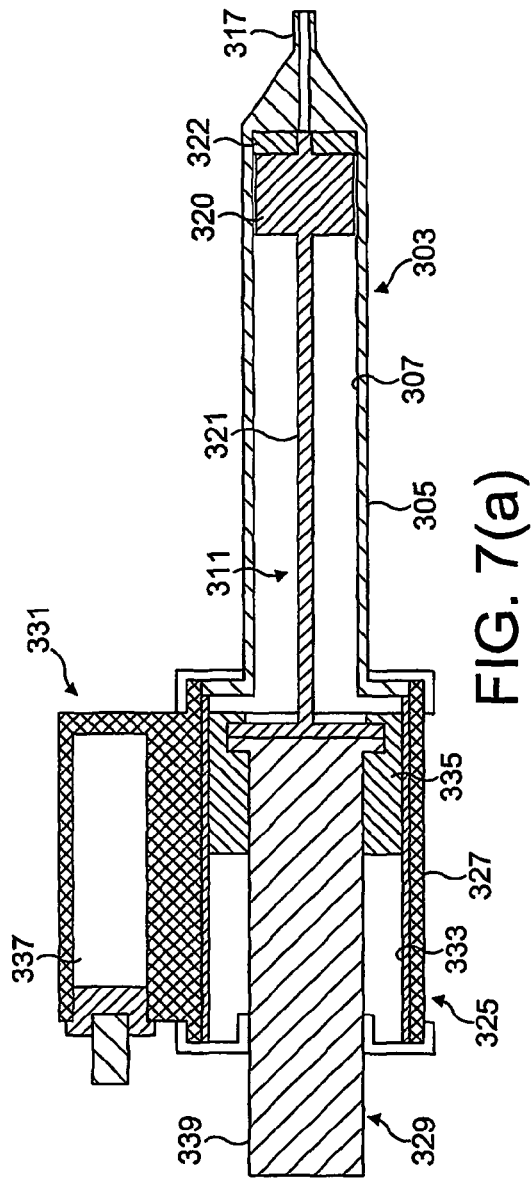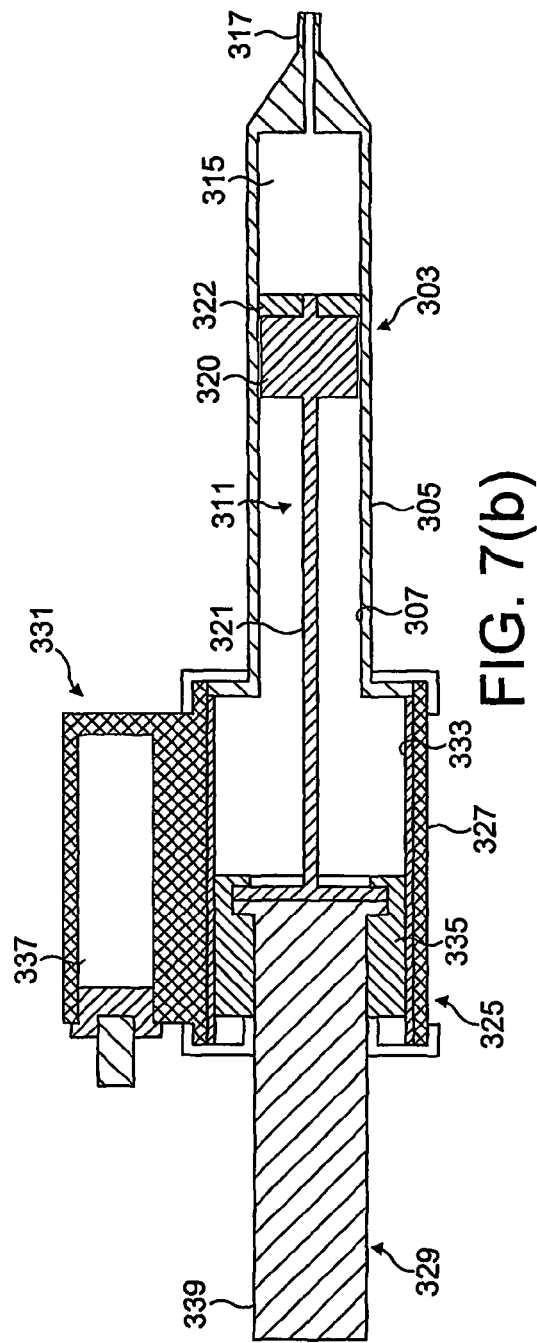
FIG. 7(a)
FIG. 7(b)

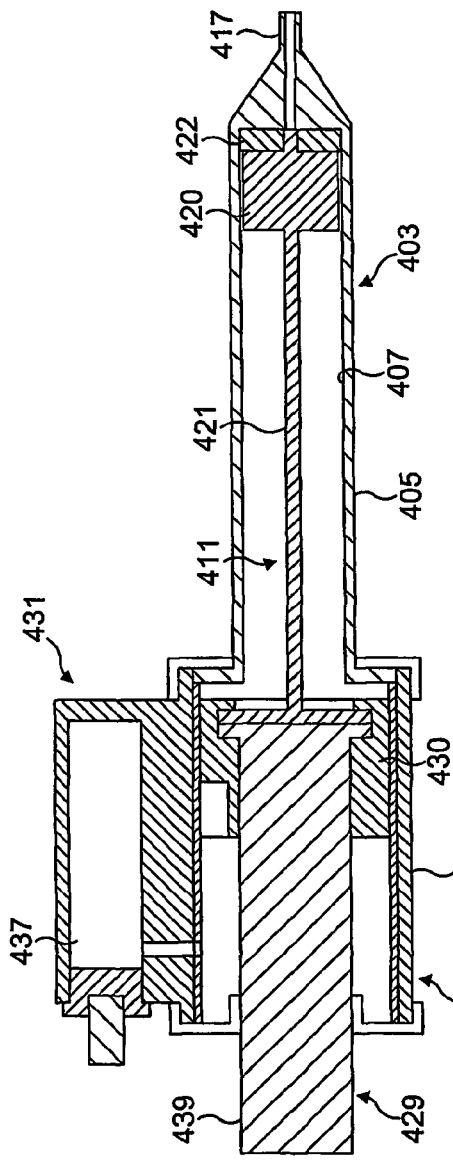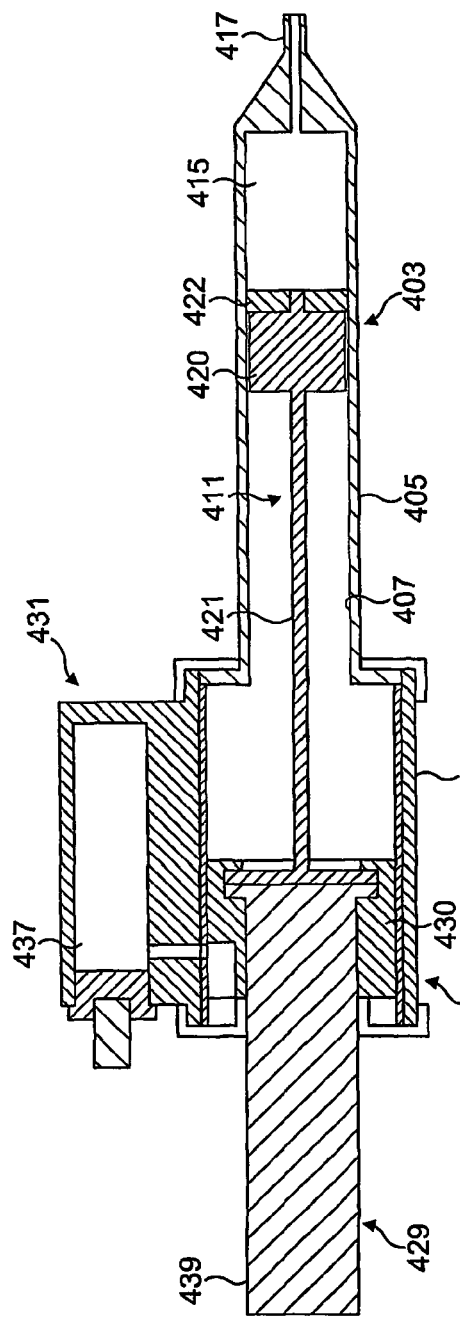

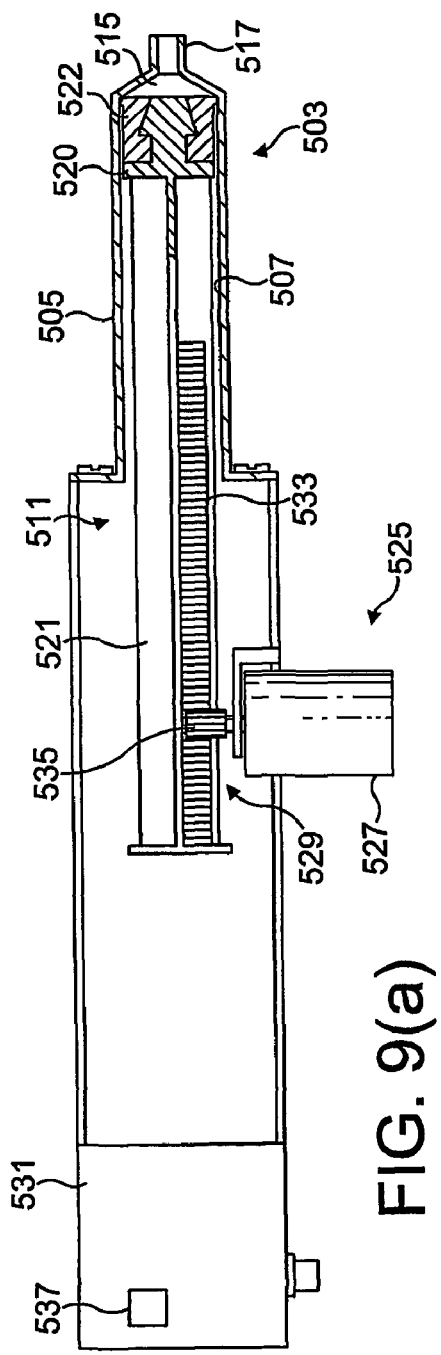
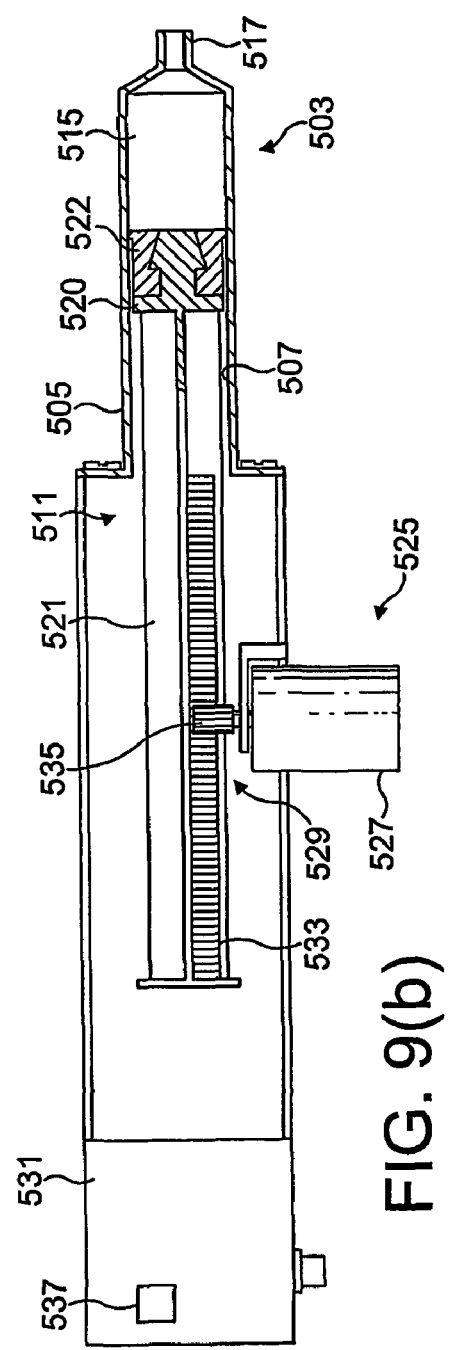
FIG. 9(a)
FIG. 9(b)

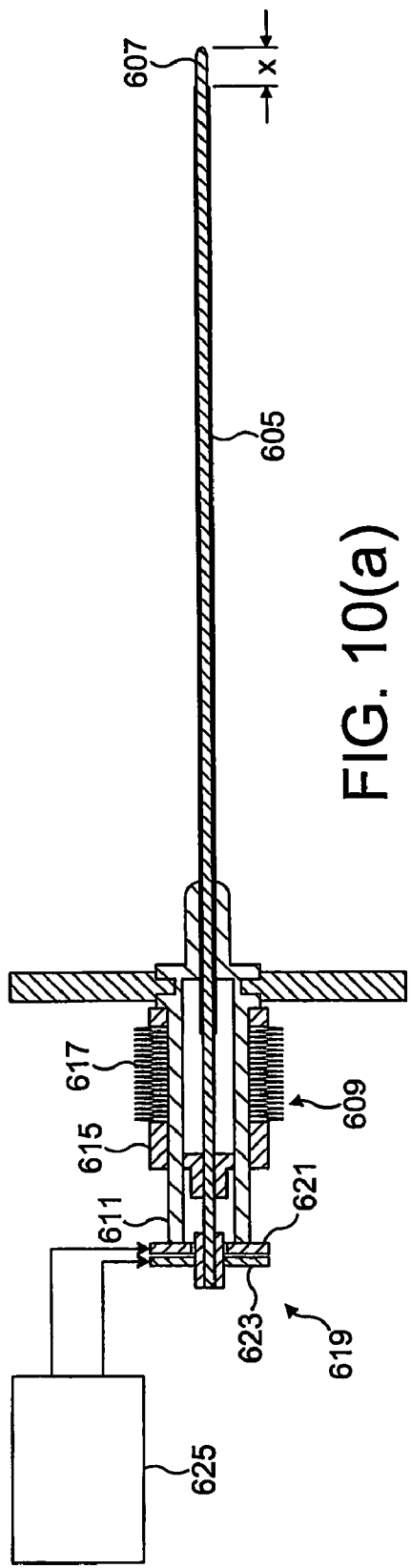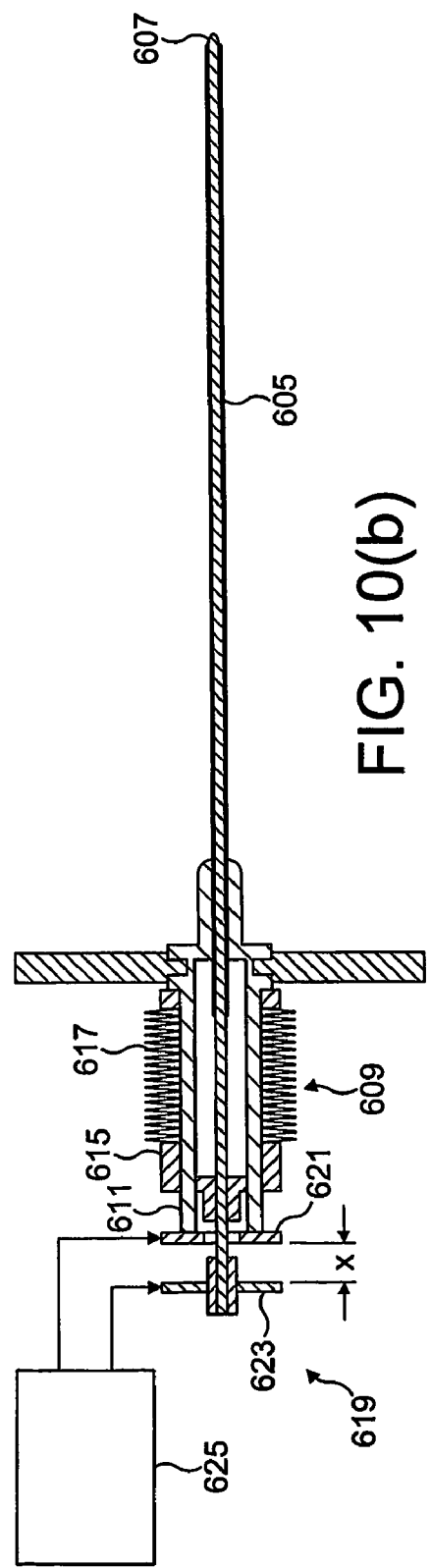

DETECTION APPARATUS AND METHOD

This application is the National Stage of International Application No. PCT/GB2004/000338, International Filing Date, Jan. 28, 2004, which designated the United States of America, and which international application was published under PCT Article 21(2) as WO Publication No. WO 2004/066853 A2 and which claims priority from British Application No. 0301934.6, filed Jan. 28, 2003.

BACKGROUND OF THE INVENTION

1. Field of the Invention

The present invention relates to an apparatus for, and a method of, locating a tip of a tubular element, in particular a needle, within a region, in particular the epidural space and the peritoneal cavity, of a body of a subject.

2. Brief Description of Related Developments

Epidural anaesthesia is becoming increasingly popular for a wide variety of surgical, obstetric and analgesic procedures, with indications including surgical anaesthesia, analgesia during labor and prolonged post-operative pain relief. Epidural anaesthesia requires the identification of the epidural space, which currently is performed by inserting a needle, in particular a Touhy needle, into the appropriate location in the spinal column. The epidural space is located beyond the ligamentum flavum indenting the dura, and is entered after the tip of the needle passes through the ligamentum flavum. The most commonly employed technique is the "loss of resistance" technique in which a Touhy needle, which is connected to a loss or resistance (LOR) syringe, is advanced through the layers of back tissue while actuating the syringe to apply a pressure to the contained fluid, with the location of the tip of the needle in the epidural cavity being detected by the user "feeling" the resistance to actuation of the syringe. This technique, however, requires considerable experience in order to avoid advancing the needle through the epidural space and into the dura, and is made particularly difficult by the user having to concentrate separately both on actuating the syringe and inserting the needle. Puncturing of the dura has been identified inter alia as the cause of chronic back pain.

Laparascopy is also being increasingly utilized, and requires the Identification of the peritoneal cavity, which currently is performed by the introduction of a Veress needle through the abdomen and into the peritoneal cavity for insufflation to produce pneumoperitoneum. As with the identification of the epidural space, the successful identification of the peritoneal cavity requires considerable experience. Identification of the peritoneal cavity is particularly difficult as the sharpness of the Veress needle does not readily allow for differentiation between layers of high and low resistance when passing the Veress needle through the abdominal layers. It is not uncommon to require very many attempts to identify the peritoneal cavity, often more than ten attempts. Furthermore, successful insertion of the Veress needle can only be determined on insufflation of the peritoneal cavity.

Apparatuses have been devised for use in detecting the epidural space, such as disclosed in U.S. Pat. No. 5,024,662, but these apparatuses, in utilizing elastic elements to bias the plunger of a delivery syringe do not allow for reliable identification of the epidural space.

SUMMARY OF THE INVENTION

It is thus an aim of the present invention to provide an improved detection apparatus and method which allows for the reliable location of a tip of a tubular element in the epidural space, and also a detection apparatus and method which allows for the reliable location of a tip of a tubular element in the peritoneal cavity.

In one aspect the present invention provides a detection apparatus for use in locating a tip of a tubular element, in particular a needle, within a region, in particular one of the epidural space and the peritoneal cavity, of a body of a subject, the delivery apparatus comprising: a biasing unit operative to maintain a biasing force to a fluid contained in a delivery unit connected in use to the tubular element, such as to cause the delivery unit to deliver fluid to the tubular element when the biasing force is greater than a resistance to flow of the fluid from the tip of the tubular element as when located within the region.

In another aspect the present invention provides a detection apparatus for use in locating a tip of a tubular element, in particular a needle, within a region, in particular one of the epidural space and the peritoneal cavity, of a body of a subject, the detection apparatus comprising: a biasing unit operative to maintain a substantially constant biasing force to any volume of fluid contained in a delivery unit connected in use to the tubular element, such as to cause the delivery unit to deliver fluid from the tubular element when the biasing force is greater than a resistance to flow of the fluid from the tip of the tubular element as when located within the region.

In a further aspect the present invention provides a detection apparatus for use in locating a tip of a tubular element, in particular a needle, within a region, in particular one of the epidural space and the peritoneal cavity, of a body of a subject, the detection apparatus comprising: a delivery unit for containing a volume of fluid and connected in use to the tubular element; and a spring element operative to maintain a biasing force to the fluid contained in the delivery unit, such as to cause the delivery unit to deliver fluid from the tubular element when the biasing force is greater than a resistance to flow of the fluid from the tip of the tubular element as when located within the region.

In a yet further aspect the present invention provides a detection apparatus for use in locating a tip of a tubular element, in particular a needle, within a region, in particular one of the epidural space and the peritoneal cavity, of a body of a subject, the detection apparatus comprising: a delivery unit comprising a body which includes a cavity and an outlet through which a fluid is deliverable and to which the tubular element is connected, and a plunger which is movably disposed in the cavity such that fluid is drawn into the fluid chamber on withdrawal of the plunger and expelled therefrom on depression of the plunger, wherein the plunger includes a shaft which includes an elongate cavity therein for housing a needle element of a needle unit for use with the apparatus.

In yet another aspect the present invention provides a detection apparatus for use in locating a tip of a tubular element, in particular a needle, within a region, in particular one of the epidural space and the peritoneal cavity, of a body of a subject, the detection apparatus comprising: a delivery unit comprising a body which includes a cavity and an outlet through which a fluid is deliverable and to which the tubular element is connected, and a plunger which is movably disposed in the cavity such that fluid is drawn into the fluid chamber on withdrawal of the plunger and expelled therefrom on depression of the plunger, wherein the plunger includes a delivery channel extending to a forward end thereof to allow for the delivery of a substance to the outlet of the body through the plunger, and a valve unit for providing only for one-way delivery of a substance through the delivery channel to the outlet of the body.

In still another aspect the present invention provides a detection apparatus for locating a tip of a tubular element, in particular a needle, within a region, in particular one of the epidural space and the peritoneal cavity, of a body of a subject, the detection apparatus comprising: a tubular element having a tip for insertion into body tissue; a sensing element extending through the tubular element and having a blunt tip; and a biasing unit for biasing the sensing element with a biasing force such that the tip of the sensing element is biased outwardly of the tip of the tubular element, whereby, when the resistance at the tip of the tubular element is greater than the biasing force, the sensing element remains stationary relative to the tubular element, and, when the resistance at the tip of the tubular element is less than the biasing force, the tip of the sensing element extends from the tip of the tubular element.

In still yet another aspect the present invention provides a method of locating a tip of a tubular element, in particular a needle, within a region, in particular one of the epidural space and the peritoneal cavity, of a body of a subject, the method comprising the steps of: connecting a detection apparatus to the tubular element, wherein the detection apparatus comprises a delivery unit which contains a fluid and is connected to the tubular element, and a biasing unit which is operable to maintain a biasing force on the fluid contained in the delivery unit which is such as to cause the delivery unit to deliver fluid therefrom when the biasing force is greater than a resistance to flow of the fluid from the tip of the tubular element as when located within the region; operating the biasing unit to maintain the biasing force on the fluid contained in the delivery unit; and progressively inserting the tubular element into the body of the subject until the biasing force acts to cause fluid to be delivered from the delivery unit through the tubular element, at which position the tip of the tubular element is within the region and the biasing force is greater than a resistance to flow of the fluid from the tip of the tubular element.

In a still yet further aspect the present invention provides a method of locating a tip of a tubular element, in particular a needle, within a region, in particular one of the epidural space and the peritoneal cavity, of a body of a subject, the method comprising the steps of: providing a detection apparatus comprising a tubular element having a tip for insertion into body tissue, a sensing element extending through the tubular element and having a blunt tip, and a biasing element for biasing the sensing element with a biasing force such that the tip of the sensing element is biased in a direction outwardly of the tip of the tubular element, the biasing element being such that, when the resistance at the tip of the tubular element is greater than the biasing force, the sensing element remains stationary relative to the tubular element, and, when the resistance at the tip of the tubular element is less than the biasing force, the tip of the sensing element extends from the tip of the tubular element; and progressively inserting the tubular element into the body of the subject until the biasing force acts to cause the tip of the sensing element to extend from the tubular element, at which position the tip of the tubular element is within the region.

The present invention assists in significantly improving both the speed and reliability of positioning the tip of a tubular element at a desired region in the body of a subject, notably the epidural space and the peritoneal cavity, and thereby provides for more successful identification of such regions.

BRIEF DESCRIPTION OF DRAWINGS

Preferred embodiments of the present invention will now be described hereinbelow by way of example only with reference to the accompanying drawings, in which:

FIG. 1(a) illustrates a longitudinal sectional view of a detection apparatus in accordance with a first embodiment of the present invention;

FIG. 1(b) illustrates a longitudinal sectional view of the detection apparatus of FIG. 1(a) in the operative state;

FIG. 2(a) illustrates a longitudinal sectional view of a detection apparatus in accordance with a second embodiment of the present invention where co-packaged with a needle unit;

FIG. 2(b) illustrates a longitudinal sectional view of the detection apparatus of FIG. 2(a) with the needle unit removed therefrom;

FIG. 4(a) illustrates a longitudinal sectional view of a detection apparatus in accordance with a fourth embodiment of the present invention;

FIG. 4(b) illustrates a longitudinal sectional view of the detection apparatus of FIG. 4(a) in the operative state;

FIG. 5(a) illustrates a longitudinal sectional view of a detection apparatus in accordance with a fifth embodiment of the present invention;

FIG. 5(b) illustrates a longitudinal sectional view of the detection apparatus of FIG. 5(a) in the operative state;

FIG. 6(a) illustrates a longitudinal sectional view of a detection apparatus in accordance with a sixth embodiment of the present invention;

FIG. 6(b) illustrates a longitudinal sectional view of the detection apparatus of FIG. 6(a) in the operative state;

FIG. 7(a) illustrates a longitudinal sectional view of a detection apparatus in accordance with a seventh embodiment of the present invention;

FIG. 7(b) illustrates a longitudinal sectional view of the detection apparatus of FIG. 7(a) in the operative state;

FIG. 8(a) illustrates a longitudinal sectional view of a detection apparatus in accordance with an eighth embodiment of the present invention;

FIG. 8(b) illustrates a longitudinal sectional view of the detection apparatus of FIG. 8(a) in the operative state;

FIG. 9(a) illustrates a longitudinal sectional view of a detection apparatus in accordance with a ninth embodiment of the present invention;

FIG. 9(b) illustrates a longitudinal sectional view of the detection apparatus of FIG. 9(a) in the operative state;

FIG. 10(a) illustrates a longitudinal sectional view of a detection apparatus in accordance with a tenth embodiment of the present invention; and FIG. 10(b) illustrates a longitudinal sectional view of the detection apparatus of FIG. 10(a) in the operative state.

DETAILED DESCRIPTION OF THE EXEMPLARY EMBODIMENTS

Figure 3A:
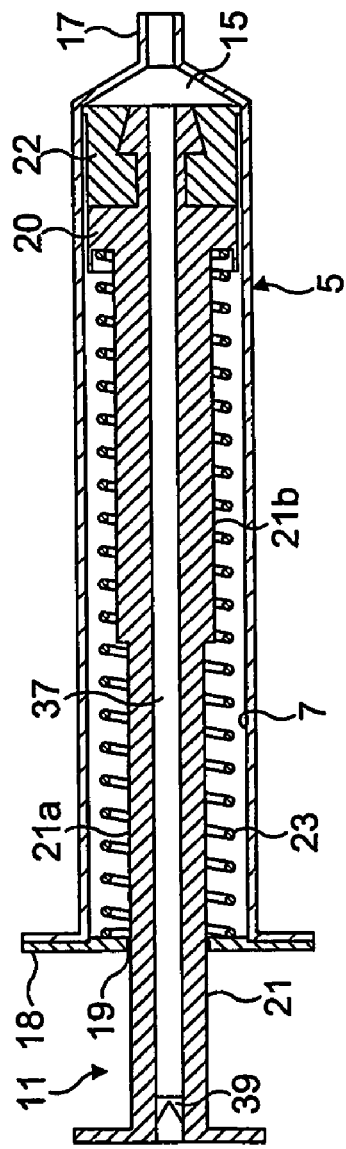
FIG. 3(a) illustrates a longitudinal sectional view of a detection apparatus in accordance with a third embodiment of the present invention.

FIGS. 1(a) and (b) illustrate a detection apparatus in accordance with a first embodiment of the present invention for detecting the location of the tip of a tubular element, in particular a needle, within a region, in particular the epidural space and the peritoneal cavity, of a body of a subject.

The apparatus comprises a body 5 which includes an elongate cavity 7, in this embodiment having a diameter of 0.6 inches, and a plunger 11 which is movably disposed in the cavity 7 and together with the cavity 7 defines a fluid chamber 15 forward of the plunger 11 for containing a fluid, in this embodiment a liquid, typically a saline solution. In this embodiment the body 5 and the plunger 11 are configured as a loss of resistance (LOR) syringe and define a delivery unit.

The body 5 includes an outlet 17 at a forward end thereof through which a fluid is deliverable and to which a needle (not illustrated) is connected, and a stop member 18 at the rear end thereof which includes an aperture 19 through which extends the plunger 11.

The plunger 11 comprises a head 20, an elongate shaft 21 which extends rearwardly of the head 20, and a gasket seal 22 which is attached to the head 20 for providing a fluid-tight seal with the cavity 7 of the body 5, such as to enable fluid to be drawn into the fluid chamber 15 on withdrawal of the plunger 11 and expelled from the fluid chamber 15 on depression of the plunger 11.

In this embodiment the shaft 21 includes a first, rear section 21a of a diametral dimension which is smaller than the aperture 19 of the stop member 18 such as to allow the rear section 21a to freely pass through the aperture 19 in the stop member 18, and a second, forward section 21b which has a diametral dimension greater than the aperture 19 in the stop member 18 such as to prevent the plunger 11 from being withdrawn beyond a predetermined extent from the body 5.

The apparatus further comprises a biasing element 23, in this embodiment a resilient element, here a compression spring, which acts to bias the plunger 11 such as to act to depress the same with a predetermined biasing force, and thereby maintain a fluid contained in the fluid chamber 15 at a predetermined pressure. The pressure is preferably not greater than about 8.5 $lbin^{-2}$, more preferably from about 0.5 $lbin^{-2}$ to about 8.5 $lbin^{-2}$, still more preferably from about 0.5 $lbin^{-2}$ to about 5.66 $lbin^{-2}$, yet more preferably from about 2.0 $lbin^{-2}$ to about 5.66 $lbin^{-2}$, and still yet more preferably from about 2.0 $lbin^{-2}$ to about 3.5 $lbin^{-2}$.

In this embodiment the biasing element 23 is disposed about the shaft 21 of the plunger 11 within the cavity 7 of the body 5 and acts between the head 20 of the plunger 11 and the stop member 18 of the body 5. In this embodiment the biasing element 23 is configured such as to provide a substantially constant biasing force over the entire operative stroke of the plunger 11, in this embodiment to maintain a fluid contained in the fluid chamber 15 at a pressure of about 2.83 $lbin^{-2}$. Through providing a constant biasing force, the present inventors have identified that the detection apparatus provides for the more reliable detection of expandable body regions. In providing a constant biasing force, the user can himself/herself select the volume of fluid to be delivered, and ensure that that volume of fluid is delivered in its entirety. For epidural application, by virtue of this complete delivery of the fluid, the fluid can be the epidural anaesthetic.

With this configuration, the biasing element 23 maintains the predetermined biasing force on the plunger 11 such that, when the resistance at the outlet 17 of the body 5 is greater than the biasing force, such as when the tip of the needle is located in body tissue which provides a relatively high flow resistance to the contained fluid, the plunger 11 remains stationary, but, when the resistance at the outlet 17 of the body 5 is less than the biasing force, such as when the tip of the needle is located in an expandable region in the body of a subject, the plunger 11 is depressed by the biasing force into the body 5 such as to deliver fluid from the fluid chamber 15.

In operation, the plunger 11 is first withdrawn from the body 5 such as to draw a volume of fluid, typically from 2 to 7 ml, and preferably from 2 to 3 ml, into the fluid chamber 15 ahead of the plunger 11, as illustrated in FIG. 1(b). Whilst holding the shaft 21 of the plunger 11 in the withdrawn position, the outlet 17 of the body 5 is connected to a needle, which has been partially pre-inserted into a subject. The needle is typically a Touhy needle for epidural application and a Veress needle for peritoneal application. Once the outlet 17 of the body 5 is connected to the needle, the shaft 21 of the plunger 11 is released. At this point, the plunger 11 remains stationary, as the tip of the needle will be located in body tissue and the flow resistance at the tip of the needle will be greater than the biasing force of the biasing element 23. The needle is then slowly advanced, typically a millimeter at a time, until such point as the tip of the needle enters an expandable region in the body of the subject, at which point the flow resistance at the tip of the needle is less than the biasing force of the biasing element 23 and the biasing element 23 acts to depress the plunger 11 into the cavity 7 of the body 5 and expel fluid from the fluid chamber 15 into the expandable region. This expulsion of fluid from the fluid chamber 15 is indicative of the tip of the needle being located in a desired expandable region of the body of the subject, such regions including the epidural space and the peritoneal cavity. Following location of the tip of the needle in the desired expandable region, the detection apparatus is then disconnected from the needle to allow for the delivery of the appropriate substance through the needle to the body region, typically an epidural anaesthetic for epidural application and an insufflation gas, such as carbon dioxide, for peritoneal application.

In alternative embodiments the extent to which the plunger 11 can be withdrawn from the body 5 could be determined by full compression of the biasing element 23 or engagement with the head 20 of the plunger 11.

FIGS. 2(a) and (b) illustrate a detection apparatus in accordance with a second embodiment of the present invention for detecting the location of the tip of a tubular element, in particular a needle, within a region, in particular the epidural space, of a body of a subject.

The apparatus of this embodiment is very similar to the apparatus of the above-described first-embodiment, and thus, in order to avoid unnecessary duplication of description, only the differences will be described in detail, with like parts being designated by like reference signs.

The apparatus of this embodiment differs from that of the above-described first embodiment in that the shaft 21 of the plunger 11 includes an elongate cavity 25 which is open at the rear end of the shaft 21, and in further comprising a needle unit 27 which is located in the cavity 25 when packaged.

The needle unit 27 comprises a tubular needle 29, in this embodiment a Touhy needle, which, when packaged, is located in the cavity 25 in the shaft 21 of the plunger 11 and a connector element 31 which is attached to one, the rear, end of the needle 29 and includes a first connector 33 by which the needle unit 27 is connected to the shaft 21 when packaged and a second connector 35, in this embodiment a catheter connector, which in use provides for connection to the outlet 17 of the body 5.

The apparatus of this embodiment is particularly advantageous in allowing for the co-packaging of the needle unit 27, and also enabling co-sterilization. Traditionally, the needle unit 27 would be sterilized and packaged independently, with the packaging be relatively expensive in requiring a rigid, shielding component to shield the needle.

Operation of the apparatus of this embodiment is the same as for the above-described first embodiment, where the needle unit 27 is removed from the shaft 21 of the plunger 11 on use, as illustrated in FIG. 2(b).

FIGS. 3(a) and (b) illustrate a detection apparatus in accordance with a third embodiment of the present invention for detecting the location of the tip of a tubular element, in particular a needle, within a region, in particular the epidural space and the peritoneal cavity, of a body of a subject.

The apparatus of this embodiment is very similar to the apparatus of the above-described first-embodiment, and thus, in order to avoid unnecessary duplication of description, only the differences will be described in detail, with like parts being designated by like reference signs.

The apparatus of this embodiment differs from that of the above-described first embodiment in that the plunger 11 includes a delivery channel 37 which extends therethrough from the forward end of the head 20 to the rear end of the shaft 21, and a valve 39 which provides for the one-way delivery of a substance through the plunger 11 to the outlet 17 of the body 5, thereby allowing for the delivery of a substance, other than the detection fluid as first contained in the fluid chamber 15, through an attached needle without requiring disconnection of the apparatus. Such substances include an epidural anaesthetic for epidural application and an insufflation gas, such as carbon dioxide, for peritoneal application.

In this embodiment the valve 39 is a one-way gasket valve, which allows for the delivery of a substance through the delivery channel 37 to the outlet 17 of the body 5, but prevents the back-flow of a substance through the plunger 11 in the opposite direction, that is, from the rear end of the shaft 21 of the plunger 11. In an alternative embodiment the valve 39 could comprise a rupturable element which is ruptured in fitting a connector to deliver a substance through the delivery channel 37 to the outlet 17 of the body 5.

The apparatus of this embodiment is particularly advantageous in enabling the delivery of a substance to the detected body region without requiring disconnection of the apparatus from the needle when the tip of the needle is located in the desired location in the body region.

Figure 3B:
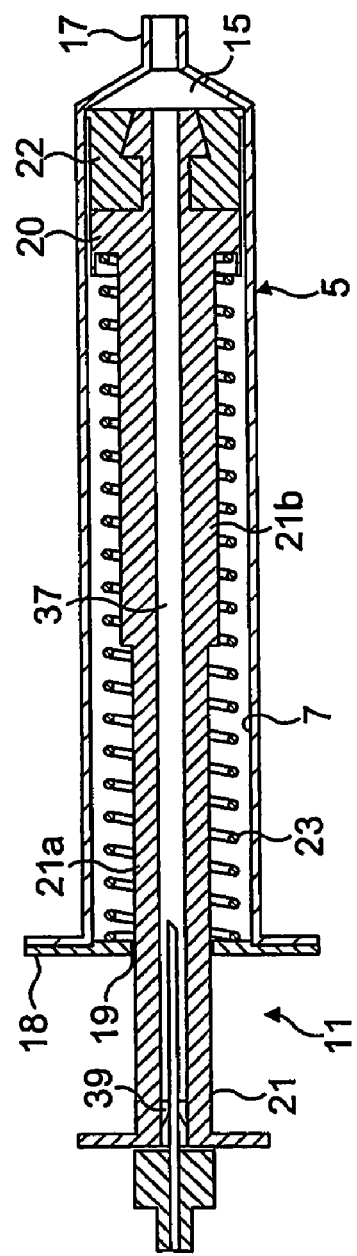
FIG. 3(b) illustrates a longitudinal sectional view of the detection apparatus of FIG. 3(a) with a connector connected to the valve unit thereof for the delivery of a substance through the detection apparatus.

Operation of the apparatus of this embodiment is the same as for the above-described first embodiment, except that the apparatus is not disconnected from the needle following insertion. Rather, following insertion of the needle, a substance is delivered through the delivery channel 37 of the apparatus to the needle without disconnection of the apparatus, as illustrated in FIG. 3(b).

FIGS. 4(a) and (b) illustrate a detection apparatus in accordance with a fourth embodiment of the present invention for detecting the location of the tip of a tubular element, in particular a needle, within a region, in particular the epidural space and the peritoneal cavity, of a body of a subject.

The apparatus of this embodiment is quite similar to the apparatus of the above-described first embodiment, and thus, in order to avoid unnecessary duplication of description, only the differences will be described in detail, with like parts being designated by like reference signs.

The apparatus of this embodiment differs from that of the above-described first embodiment in that the plunger 11 does not include a gasket seal 22, and in further comprising a separate variable-volume container 41 which is disposed forwardly of the head 20 of the plunger 11 in the cavity 7 of the body 5 and fluidly connected to the outlet 17 of the body 5. In this embodiment the container 41 defines the fluid chamber 15 and together with the body 5 and the plunger 11 defines a delivery unit, with a fluid being drawn into the container 41 on expansion thereof and expelled from the container 41 on compression thereof.

In this embodiment the container 41 comprises a flexible, tubular bellows structure which is attached to the forward end of the head 20 of the plunger 11, such as to be operable by the same between a compressed state, as illustrated in FIG. 4(a), and an expanded state, as illustrated in FIG. 4(b).

In one alternative embodiment the container 41 could comprise a resilient, tubular bellows structure which is configured to expand to the expanded state in the absence of the application of a biasing force thereto by the plunger 11, with the effective biasing force of the main biasing element 23 being configured such as to achieve the required fluid pressure at the outlet 17 of the body 5. In this embodiment the bellows structure need not be attached to the plunger 11.

In another alternative embodiment the container 41 could comprise a flexible, tubular bellows structure and a separate biasing element which is configured to expand the bellows structure to the expanded state in the absence of the application of a biasing force thereto by the plunger 11, with the effective biasing force of the main biasing element 23 being configured such as to achieve the required fluid pressure at the outlet 17 of the body 5. In this embodiment the bellows structure need not be attached to the plunger 11.

Operation of the apparatus of this embodiment is the same as for the above-described first embodiment, where FIG. 4(b) illustrates the plunger 11 when withdrawn as ready for use in detecting the location of the tip of a needle, with the container 41 being in the expanded state.

FIGS. 5(a) and (b) illustrate a detection apparatus in accordance with a fifth embodiment of the present invention for detecting the location of the tip of a tubular, element, in particular a needle, within a region, in particular the epidural space and the peritoneal cavity, of a body of a subject.

The apparatus comprises a body 105 which includes a cavity 107 and an outlet 109 which is fluidly connected to the cavity 107, through which a fluid, in this embodiment a liquid, typically a saline solution, is deliverable and to which a needle (not illustrated) is connected, and a variable-volume container 111 which is fluidly connected to the cavity 107 and together with the cavity 107 defines a fluid chamber 115 for containing a fluid, with a fluid being drawn into the fluid chamber 115 on expansion of the container 111 to an expanded state and expelled from the fluid chamber 115 on contraction of the container 111 to a contracted state. In this embodiment the body 105 and the container 111 define a delivery unit.

The apparatus further comprises a grip member 117 which is attached to the container 111, in this embodiment the rear end thereof, and is gripped by a user to expand the container 111 to the expanded state and draw a fluid into the fluid chamber 115, with the grip member 117 enabling the user to maintain the container 111 in the expanded state until the outlet 109 of the body 105 is connected to a needle. In this embodiment the grip member 117 comprises an annular sleeve which encloses the container 111 and is slideably disposed to the body 105.

In this embodiment the container 111 comprises a resilient, tubular bellows structure which is configured such as normally to be under tension and acts to contract to the contracted state, thereby acting as a biasing unit and applying a predetermined biasing force to a fluid contained in the fluid chamber 115, with the biasing force being such that a fluid contained in the fluid chamber 115 is at a predetermined pressure. The pressure is preferably not greater than about 8.5 $lbin^{-2}$, more preferably from about 0.5 $lbin^{-2}$ to about 8.5 $lbin^{-2}$, still more preferably from about 0.5 $lbin^{-2}$ to about 5.66 $lbin^{-2}$, yet more preferably from about 2.0 $lbin^{-2}$ to about 5.66 $lbin^{-2}$, and still yet more preferably from about 2.0 $lbin^{-2}$ to about 3.5 $lbin^{-2}$.

In this embodiment the container 111 is configured such as to provide a substantially constant biasing force over the entire operative extension thereof, in this embodiment to maintain a fluid contained in the fluid chamber 115 at a pressure of about 2.83 lbin$^{-2}$. Through providing a constant biasing force, the present inventors have identified that the detection apparatus provides for the more reliable detection of expandable body regions.

In an alternative embodiment the container 111 could comprise a flexible, tubular bellows structure and a separate biasing element, such as tension spring, which is configured to contract the bellows structure to the contracted state, with the biasing force of the separate biasing element being such that a fluid contained in the fluid chamber 115 is at a predetermined pressure.

With this configuration, the biasing force applied to a fluid contained in the fluid chamber 115 is such that, when the resistance at the outlet 109 of the body 105 is greater than the biasing force, such as when the tip of the needle is located in body tissue which provides a relatively high flow resistance to the contained fluid, the container 111 remains in the expanded state, but, when the resistance at the outlet 109 of the body 105 is less than the biasing force, such as when the tip of the needle is located in an expandable region in the body of a subject, the container 111 contracts such as to deliver fluid from the fluid chamber 115 through the outlet 109 of the body 105.

In operation, the grip member 117 is first withdrawn such as to draw a volume of a fluid, typically 2 to 7 ml, and preferably 2 to 3 ml, into the fluid chamber 115, as illustrated in FIG. 5(b). In a preferred embodiment at least 1 ml of fluid is to be delivered. Whilst holding the grip member 117 in the withdrawn position, the outlet 109 of the body 105 is connected to a needle, which has been partially pre-inserted into a subject. The needle is typically a Touhy needle for epidural application and a Veress needle for peritoneal application. Once the outlet 109 of the body 105 is connected to the needle, the grip member 117 is released. At this point, the container 111 remains in the expanded state, as the tip of the needle will be located in body tissue and the flow resistance at the tip of the needle will be greater than the biasing force as applied by the container 111. The needle is then slowly advanced, typically a millimeter at a time, until such point as the tip of the needle enters an expandable region in the body of the subject, at which point the flow resistance at the tip of the needle is less than the biasing force as applied by the container 111, and the container 111 contracts, expelling fluid from the fluid chamber 115 through the outlet 109 of the body 105 and into the expandable region. This expulsion of fluid from the fluid chamber 115 is indicative of the tip of the needle being located in a desired expandable region of the body of the subject, such regions including the epidural space and the peritoneal cavity. Following location of the tip of the needle in the desired expandable region, the detection apparatus is then disconnected from the needle to allow for the delivery of the appropriate substance through the needle to the body region, typically an epidural anaesthetic for epidural application and an insufflation gas, such as carbon dioxide, for peritoneal application.

FIGS. 6(a) and (b) illustrate a detection apparatus in accordance with a sixth embodiment of the present invention for detecting the location of the tip of a tubular element, in particular a needle, within a region, in particular the epidural space and the peritoneal cavity, of a body of a subject.

The apparatus comprises a delivery unit 203 which is actuatable to deliver a fluid, in this embodiment a liquid, typically a saline solution.

The delivery unit 203, in this embodiment as a loss of resistance (LOR) syringe, comprises a body 205 which includes an elongate cavity 207, and a plunger 211 which is movably disposed in the cavity 207 and together with the cavity 207 defines a fluid chamber 215 forward of the plunger 211 for containing a fluid, in this embodiment a liquid, typically a saline solution.

The body 205 includes an outlet 217 at a forward end thereof through which a fluid is deliverable and to which a needle (not illustrated) is connected.

The plunger 211 comprises a head 220, an elongate shaft 221 which extends rearwardly of the head 220, and a gasket seal 222 which is attached to the head 220 for providing a fluid-tight seal with the cavity 207 of the body 205, such as to enable a fluid to be drawn thereinto on withdrawal of the plunger 211 and expelled therefrom on depression of the plunger 211.

The apparatus further comprises a biasing unit 225 which is coupled to the delivery unit 203 such as to bias the plunger 211 of the delivery unit 203 with a predetermined biasing force into the body 205 thereof.

The biasing unit 225 comprises a body 227 which is coupled to the body 205 of the delivery unit 203, a drive member 229 which is movably disposed to the body 227 and connected to the plunger 211 of the delivery unit 203 such as to provide for movement of the plunger 211 on movement of the drive member 229, and a biasing element 231, in this embodiment a resilient element, such as a compression spring, which is such as normally to bias the drive member 229, and hence the plunger 211 of the delivery unit 203, with a predetermined biasing force, and thereby maintain a fluid contained in the fluid chamber 215 at a predetermined pressure. The pressure is preferably not greater than about 8.5 lbin$^{-2}$, more preferably from about 0.5 lbin$^{-2}$ to about 8.5 lbin$^{-2}$, still more preferably from about 0.5 lbin$^{-2}$ to about 5.66 lbin$^{-2}$, yet more preferably from about 2.0 lbin$^{-2}$ to about 5.66 lbin$^{-2}$, and still yet more preferably from about 2.0 lbin$^{-2}$ to about 3.5 lbin$^{-2}$.

In this embodiment the biasing element 231 is configured such as to provide a substantially constant biasing force over the entire stroke of the plunger 211, in this embodiment to maintain a fluid contained in the fluid chamber 215 at a pressure of about 2.83 lbin$^{-2}$. Through providing a constant biasing force, the present inventors have identified that the detection apparatus provides for the more reliable detection of expandable body regions.

With this configuration, the biasing element 231 maintains a predetermined biasing force on the plunger 211 of the delivery unit 203 such that, when the resistance at the outlet 217 of the delivery unit 203 is greater than the biasing force, such as when the tip of the needle is located in body tissue which provides a relatively high flow resistance to the contained fluid, the plunger 211 remains stationary, but, when the resistance at the outlet 217 of the delivery unit 203 is less than the biasing force, such as when the tip of the needle is located in an expandable region in the body of a subject, the plunger 211 is driven by the biasing force into the body 205 of the delivery unit 203 such as to deliver fluid from the fluid chamber 215 and through the outlet 217 of the delivery unit 203.

In this embodiment the drive member 229 is fixed to the plunger 211 of the delivery unit 203 and includes a grip 233 which allows for manual operation by a user, and, in particular, movement of the drive member 229 such as to withdraw the plunger 211 from the body 205 of the delivery unit 203 and thereby enable fluid to be drawn into the fluid chamber 215 of the delivery unit 203 ahead of the plunger 211, and also allow for the biasing unit 225 to be held in an inoperative position until the outlet 217 of the delivery unit 203 is connected to a needle.

In operation, the biasing unit 225 is coupled to the delivery unit 203, and the drive member 229 of the biasing unit 225 is withdrawn such as to draw a volume of a fluid, typically 2 to 7 ml, and preferably 2 to 3 ml, into the fluid chamber 215 of the delivery unit 203 ahead of the plunger 211, as illustrated in FIG. 6(b). Whilst holding the drive member 229 in the withdrawn position, in this embodiment by holding the grip 233, the outlet 217 of the delivery unit 203 is connected to a needle, which has been partially pre-inserted into a subject. The needle is typically a Touhy needle for epidural application and a Veress needle for peritoneal application. Once the outlet 217 of the delivery unit 203 is connected to the needle, the drive member 229 of the biasing unit 225 is released. At this point, the drive member 229 of the biasing unit 225 remains stationary, as the tip of the needle will be located in body tissue and the flow resistance at the tip of the needle will be greater than the biasing force of the biasing unit 225. The needle is then slowly advanced, typically a millimeter at a time, until such point as the tip of the needle enters an expandable region in the body of the subject, at which point the flow resistance at the tip of the needle is less than the biasing force of the biasing unit 225 and the biasing unit 225 acts to drive the plunger 211 of the delivery unit 203 into the cavity 207 of the body 205 of the delivery unit 203 and expel fluid from the fluid chamber 215 through the outlet 217 of the delivery unit 203 and into the expandable region. This expulsion of fluid from the fluid chamber 215 is indicative of the tip of the needle being located in a desired expandable region of the body of the subject, such regions including the epidural space and the peritoneal cavity. Following location of the tip of the needle in the desired expandable region, the detection apparatus is then disconnected from the needle to allow for the delivery of the appropriate substance through the needle to the body region, typically an epidural anaesthetic for epidural application and an insufflation gas, such as carbon dioxide, for peritoneal application.

In this embodiment the biasing unit 225 is configured such as to be detachable from the delivery unit 203 through a quick-fit coupling, and thereby provides for the use of a replacement delivery unit 203 with each procedure.

FIGS. 7(a) and (b) illustrate a detection apparatus in accordance with a seventh embodiment of the present invention for detecting the location of the tip of a tubular element, in particular a needle, within a region, in particular the epidural space and the peritoneal cavity, of a body of a subject.

The apparatus comprises a delivery unit 303 which is actuatable to deliver a fluid, in this embodiment a liquid, typically a saline solution.

The delivery unit 303, in this embodiment as a loss of resistance (LOR) syringe, comprises a body 305 which includes an elongate cavity 307, and a plunger 311 which is movably disposed in the cavity 307 and together with the cavity 307 defines a fluid chamber 315 forward of the plunger 311 for containing a fluid.

The body 305 includes an outlet 317 at a forward end thereof through which a fluid is deliverable and to which a needle (not illustrated) is connected.

The plunger 311 comprises a head 320, an elongate shaft 321 which extends rearwardly of the head 320, and a gasket seal 322 which is attached to the head 320 for providing a fluid-tight seal with the cavity 307 of the body 305, such as to enable a fluid to be drawn thereinto on withdrawal of the plunger 311 and expelled therefrom on depression of the plunger 311.

The apparatus further comprises a biasing unit 325 which is coupled to the delivery unit 303 such as to bias the plunger 311 of the delivery unit 303 with a biasing force into the body 305 thereof.

The biasing unit 325 comprises a body 327 which is coupled to the body 305 of the delivery unit 303, a drive member 329 which is movably disposed to the body 327 and connected to the plunger 311 of the delivery unit 303 such as to provide for movement of the plunger 311 on movement of the drive member 329, and an electromagnetic drive 331 which is operable to bias the drive member 329, and hence the plunger 311 of the delivery unit 303, with a predetermined biasing force, and thereby maintain a fluid contained in the fluid chamber 315 at a predetermined pressure. The pressure is preferably not greater than about 8.5 $lbin^{-2}$, more preferably from about 0.5 $lbin^{-2}$ to about 8.5 $lbin^{-2}$, still more preferably from about 0.5 $lbin^{-2}$ to about 5.66 $lbin^{-2}$, yet more preferably from about 2.0 $lbin^{-2}$ to about 5.66 $lbin^{-2}$, and still yet more preferably from about 2.0 $lbin^{-2}$ to about 3.5 $lbin^{-2}$.

In this embodiment the electromagnetic drive 331 is configured such as to provide a substantially constant biasing force over the entire operative stroke of the plunger 311, in this embodiment to maintain a fluid contained in the fluid chamber 315 at a pressure of about 2.83 $lbin^{-2}$. Through providing a constant biasing force, the present inventors have identified that the detection apparatus provides for the more reliable detection of expandable body regions.

The electromagnetic drive 331 comprises an energizable coil 333 which is disposed within the body 327 of the biasing unit 325, a magnet 335, in this embodiment an annular magnet, which is fixed to the drive member 329 and disposed within the coil 333 such as to be biased forwardly on the energization of the same, and a switch-operated power source 337, in this embodiment a battery, for energizing the coil 333.

In an alternative embodiment the energizable coil 333 could be disposed to the drive member 329 of the biasing unit 325 and the magnet 335 disposed to the body 327 of the biasing unit 325.

In another alternative embodiment the energizable coil 333 could be replaced by a magnet such as to provide a magnetic drive.

With this configuration, the electromagnetic drive 331 is operative to maintain a predetermined biasing force on the plunger 311 of the delivery unit 303 such that, when the resistance at the outlet 317 of the delivery unit 303 is greater than the biasing force, such as when the tip of the needle is located in body tissue which provides a relatively high flow resistance to the fluid at the outlet 317 of the delivery unit 303, the plunger 311 of the delivery unit 303 remains stationary, but, when the resistance at the outlet 317 of the delivery unit 303 is less than the biasing force, such as when the tip of the needle is located in an expandable region in the body of a subject, the plunger 311 of the delivery unit 303 is driven by the biasing force into the cavity 307 in the body 305 of the delivery unit 303 to expel fluid from the fluid chamber 315 through the outlet 317 of the delivery unit 303 and into the expandable region.

In this embodiment the drive member 329 of the biasing unit 325 is fixed to the plunger 311 of the delivery unit 303 and includes a grip 339 which allows for manual operation by a user, and, in particular, movement of the drive member 329 such as to withdraw the plunger 311 from the body 305 of the delivery unit 303 and thereby enable fluid to be drawn into the cavity 307 in the body 305 of the delivery unit 303 ahead of the plunger 311.

In operation, the biasing unit 325 is coupled to the delivery unit 303, and the drive member 329 of the biasing unit 325 is withdrawn such as to withdraw the plunger 311 of the delivery unit 303 and draw a volume of a fluid, typically 2 to 7 ml, and preferably 2 to 3 ml, into the fluid chamber 315 of the delivery unit 303. The outlet 317 of the delivery unit 303 is then connected to a needle, which has been partially pre-inserted into a subject. The needle is typically a Touhy needle for epidural application and a Veress needle for peritoneal application. Once the outlet 317 of the delivery unit 303 is connected to the needle, the electromagnetic drive 331 is actuated. At this point, the drive member 329 of the biasing unit 325 remains stationary, as the tip of the needle will be located in body tissue and the flow resistance at the tip of the needle will be greater than the biasing force of the electromagnetic drive 331. The needle is then slowly advanced, typically a millimeter at a time, until such point as the tip of the needle enters an expandable region in the body of the subject, at which point the flow resistance at the tip of the needle is less than the biasing force of the electromagnetic drive 331 and the electromagnetic drive 331 acts to drive the plunger 311 of the delivery unit 303 into the cavity 307 in the body 305 of the delivery unit 303 and expel fluid from the fluid chamber 315 through the outlet 317 of the delivery unit 303 and into the expandable region. This delivery of fluid from the fluid chamber 315 is indicative of the tip of the needle being located in a desired expandable region of the body of the subject, such regions including the epidural space and the peritoneal cavity. Following location of the tip of the needle in the desired expandable region, the detection apparatus is then disconnected from the needle to allow for the delivery of the appropriate substance through the needle to the body region, typically an epidural anaesthetic for epidural application and an insufflation gas, such as carbon dioxide, for peritoneal application.

In this embodiment the biasing unit 325 is configured such as to be detachable from the delivery unit 303 through a quick-fit coupling, and thereby provides for the use of a replacement delivery unit 303 with each procedure.

In an alternative embodiment the biasing unit 325 could be integrally formed with the delivery unit 303 such as to provide a single disposable/re-usable apparatus.

FIGS. 8(a) and (b) illustrate a detection apparatus in accordance with an eighth embodiment of the present invention for detecting the location of the tip of a tubular element, in particular a needle, within a region, in particular the epidural space and the peritoneal cavity, of a body of a subject.

The apparatus comprises a delivery unit 403 which is actuatable to deliver a fluid, in this embodiment a liquid, typically a saline solution.

The delivery unit 403, in this embodiment as a loss of resistance (LOR) syringe, comprises a body 405 which includes an elongate cavity 407, and a plunger 411 which is movably disposed in the cavity 407 and together with the cavity 407 defines a fluid chamber 415 forward of the plunger 411 for containing a fluid.

The body 405 includes an outlet 417 at a forward end thereof through which a fluid is deliverable and to which a needle (not illustrated) is connected.

The plunger 411 comprises a head 420, an elongate shaft 421 which extends rearwardly of the head 420, and a gasket seal 422 which is attached to the head 420 for providing a fluid-tight seal with the cavity 407 of the body 405, such as to enable a fluid to be drawn thereinto on withdrawal of the plunger 411 and expelled therefrom on depression of the plunger 411.

The apparatus further comprises a biasing unit 425 which is coupled to the delivery unit 403 such as to bias the plunger 411 of the delivery unit 403 with a predetermined biasing force into the body 405 thereof.

The biasing unit 425 comprises a body 427 which is coupled to the body 405 of the delivery unit 403, a drive member 429, including an annular piston 430 disposed at the forward end thereof, which is movably disposed in the body 427 and connected to the plunger 411 of the delivery unit 403 such as to provide for movement of the plunger 411 on movement of the drive member 429, and a pneumatic drive 431 which is operable to apply a predetermined pressure to the piston 430 of the drive member 429 and bias the drive member 429, and hence the plunger 411 of the delivery unit 403, with a predetermined biasing force, and thereby maintain a fluid contained in the fluid chamber 415 at a predetermined pressure. The pressure is preferably not greater than about 8.5 $lbin^{-2}$, more preferably from about 0.5 $lbin^{-2}$ to about 8.5 $lbin^{-2}$, still more preferably from about 0.5 $lbin^{-2}$ to about 5.66 $lbin^{-2}$, yet more preferably from about 2.0 $lbin^{-2}$ to about 5.66 $lbin^{-2}$, and still yet more preferably from about 2.0 $lbin^{-2}$ to about 3.5 $lbin^{-2}$.

In this embodiment the pneumatic drive 431 is configured such as to provide a substantially constant biasing force over the entire stroke of the plunger 411, in this embodiment to maintain a fluid contained in the fluid chamber 415 at a pressure of about 2.83 $lbin^{-2}$. Through providing a constant biasing force, the present inventors have identified that the detection apparatus provides for the more reliable detection of expandable body regions.

The pneumatic drive 431 comprises a switch-operated gas supply 437, in this embodiment a battery-powered gas supply, for supplying a gas at a predetermined pressure to the piston 430 of the drive member 429, and thereby bias the drive member 429, and hence the plunger 411 of the delivery unit 403, at the predetermined biasing force.

With this configuration, the pneumatic drive 431, when actuated, maintains a predetermined biasing force on the plunger 411 such that, when the resistance at the outlet 417 of the delivery unit 403 is greater than the biasing force, such as when the tip of the needle is located in body tissue which provides a relatively high flow resistance to the fluid at the outlet 417 of the delivery unit 403, the plunger 411 remains stationary, but, when the resistance at the outlet 417 of the delivery unit 403 is less than the biasing force, such as when the tip of the needle is located in an expandable region in the body of a subject, the plunger 411 is driven by the biasing force.

In this embodiment the drive member 429 of the biasing unit 425 is fixed to the plunger 411 of the delivery unit 403 and includes a grip 439 which allows for manual operation by a user, and, in particular, movement of the drive member 429 of the biasing unit 425 such as to withdraw the plunger 411 of the delivery unit 403 from the body 405 of the delivery unit 403 and thereby enable a fluid to be drawn into the cavity 407 in the body 405 ahead of the plunger 411.

In operation, the biasing unit 425 is coupled to the delivery unit 403, and the drive member 429 of the biasing unit 425 is withdrawn such as to draw a volume of a fluid, typically 2 to 7 ml, and preferably 2 to 3 ml, into the fluid chamber 415 of the delivery unit 403, as illustrated in FIG. 8(b). The outlet 417 of the delivery unit 403 is then connected to a needle, which has been partially pre-inserted into a subject. The needle is typically a Touhy needle for epidural application and a Veress needle for peritoneal application. Once the outlet 417 of the delivery unit 403 is connected to the needle, the pneumatic drive 431 is actuated. At this point, the drive member 429 of the biasing unit 425 remains stationary, as the tip of the needle will be located in body tissue and the flow resistance at the tip of the needle will be greater than the biasing force of the pneumatic drive 431. The needle is then slowly advanced, typically a millimeter at a time, until such point as the tip of the needle enters an expandable region in the body of the subject, at which point the flow resistance at the tip of the needle is less than the biasing force of the pneumatic drive 431 and the pneumatic drive 431 acts to drive the plunger 411 of the delivery unit 403 into the cavity 407 in the body 405 of the delivery unit 403 and expel fluid from the fluid chamber 415 through the outlet 417 of the delivery unit 403 and into the expandable region. This expulsion of fluid from the fluid chamber 415 is indicative of the tip of the needle being located in a desired expandable region of the body of the subject, such regions including the epidural space and the peritoneal cavity. Following location of the tip of the needle in the desired expandable region, the detection apparatus is then disconnected from the needle to allow for the delivery of the appropriate substance through the needle to the body region, typically an epidural anaesthetic for epidural application and an insufflation gas, such as carbon dioxide, for peritoneal application.

In this embodiment the biasing unit 425 is configured such as to be detachable from the delivery unit 403 through a quick-fit coupling, and thereby provides for the use of a replacement delivery unit 403 with each procedure.

In an alternative embodiment the biasing unit 425 could be integrally formed with the delivery unit 403 such as to provide a single disposable/re-usable detection apparatus.

In another embodiment the gas supply 437 could be a manually-primed supply, for example, as provided by a manually-operated piston.

FIGS. 9(a) and (b) illustrate a detection apparatus in accordance with a ninth embodiment of the present invention for detecting the location of the tip of a tubular element, in particular a needle, within a region, in particular the epidural space and the peritoneal cavity, of a body of a subject.

The apparatus comprises a delivery unit 503 which is actuatable to deliver a fluid, in this embodiment a liquid, typically a saline solution.

The delivery unit 503, in this embodiment as a loss of resistance (LOR) syringe, comprises a body 505 which includes an elongate cavity 507, and a plunger 511 which is movably disposed in the cavity 507 and together with the cavity 507 defines a fluid chamber 515 forward of the plunger 511 for containing a fluid.

The body 505 includes an outlet 517 at a forward end thereof through which a fluid is deliverable and to which a needle (not illustrated) is connected.

The plunger 511 comprises a head 520, an elongate shaft 521 which extends rearwardly of the head 520, and a gasket seal 522 which is attached to the head 520 for providing a fluid-tight seal with the cavity 507 of the body 505, such as to enable a fluid to be drawn thereinto on withdrawal of the plunger 511 and expelled therefrom on depression of the plunger 511.

The apparatus further comprises a biasing unit 525 which is coupled to the delivery unit 503 such as to bias the plunger 511 of the delivery unit 503 with a predetermined biasing force into the body 505 thereof.

The biasing unit 525 comprises a drive motor 527, in this embodiment a battery-powered DC motor, a geared connection 529, which operably couples the drive motor 527 to the plunger 511 of the delivery unit 503 such as to drive the same with a predetermined biasing force on operation of the drive motor 527, and control circuitry 531 for controlling the operation of the drive motor 527.

In this embodiment the biasing force applied to the plunger 511 maintains a fluid contained in the fluid chamber 515 at a predetermined pressure. The pressure is preferably not greater than about 8.5 $lbin^{-2}$, more preferably from about 0.5 $lbin^{-2}$ to about 8.5 $lbin^{-2}$, still more preferably from about 0.5 $lbin^{-2}$ to about 5.66 $lbin^{-2}$, yet more preferably from about 2.0 $lbin^{-2}$ to about 5.66 $lbin^{-2}$, and still yet more preferably from about 2.0 $lbin^{-2}$ to about 3.5 $lbin^{-2}$.

In this embodiment the biasing unit 525 is configured such as to apply a substantially constant biasing force to the plunger 511, in this embodiment to maintain a fluid contained in the fluid chamber 515 at a pressure of about 2.83 $lbin^{-2}$. Through providing a constant biasing force, the present inventors have identified that the detection apparatus provides for the more reliable detection of expandable body regions.

In this embodiment the geared connection 529 comprises a rack 533 mounted to the shaft 521 of the plunger 511 and a pinion 535 mounted to the shaft of the drive motor 527.

In this embodiment the control circuitry 531 includes a drive circuit which comprises a PIC microcontroller (as supplied by MicroChip, Inc, USA) which controls the drive motor 527 to develop a predetermined maximum torque corresponding to the required biasing force, such that, when the resistance at the outlet 517 of the delivery unit 503 is greater than the biasing force, such as when the tip of the needle is located in body tissue which provides a relatively high flow resistance to the fluid at the outlet 517 of the delivery unit 503 and the plunger 511 remains stationary, the drive motor 527 remains in a stall condition and draws a high current, but, when the resistance at the outlet 517 of the delivery unit 503 is less than the biasing force, such as when the tip of the needle is located in an expandable region in the body of a subject, the drive motor 527 enters a drive condition in which the plunger 511 is driven by the drive motor 527, with the drive motor 527 drawing only a low current in the drive condition. In this embodiment the drive circuit is configured to deactuate the drive motor 527 following the onset of the drive condition, as detected by the drive current being below a predetermined threshold value, so as thereby advantageously to require only a minimum delivery of fluid from the fluid chamber 515 into the expandable body region.

The control circuitry 531 further comprises an indicator circuit which includes an indicator 537, in this embodiment a LED, for indicating the status of location of the tip of the needle. In this embodiment the indicator circuit drives the indicator 537 to flash where the drive motor 527 is in the stall condition, that is, where the tip of the needle is located in body tissue, and be continuously illuminated where the drive motor 527 is in the drive condition, that is, where the tip of the needle is located in the required body region.

In operation, the biasing unit 525 is first actuated to withdraw the plunger 511 of the delivery unit 503 and draw a volume of a fluid, typically 2 to 7 ml, and preferably 2 to 3 ml, into the fluid chamber 515 of the delivery unit 503, as illustrated in FIG. 9(b). The outlet 517 of the delivery unit 503 is then connected to a needle, which has been partially pre-inserted into a subject. The needle is typically a Touhy needle for epidural application and a Veress needle for peritoneal application. Once the outlet 517 of the delivery unit 503 is connected to the needle, the biasing unit 525 is actuated to drive the plunger 511 of the delivery unit 503. At this point, the drive motor 527 is in the stall condition and the plunger 511 of the delivery unit 503 remains stationary, as the tip of the needle will be located in body tissue and the flow resistance at the tip of the needle will be greater than the biasing force, with the indicator 537 flashing to indicate to the user that the tip of the needle is located within body tissue. The needle is then slowly advanced, typically a millimeter at a time, until such point as the tip of the needle enters an expandable region in the body of the subject, at which point the flow resistance at the tip of the needle is less than the biasing force and the drive motor 527 enters the drive condition and acts to drive the plunger 511 of the delivery unit 503 into the cavity 507 in the body 505 of the delivery unit 503 and expel fluid from the fluid chamber 515 through the outlet 517 of the delivery unit 503 and into the expandable region. This expulsion of fluid from the fluid chamber 515 is indicative of the tip of the needle being located in a desired expandable region of the body of the subject, such regions including the epidural space and the peritoneal cavity. On the drive motor 527 entering the drive condition, as detected by the drive current being less than a predetermined threshold value, the drive motor 527 is de-actuated and the indicator 537 is continuously illuminated to indicate to the operator that the needle is correctly inserted.

In another embodiment the geared connection 529 could comprise a ball screw/lead screw arrangement, where the ball screw/lead screw has a large pitch such as to provide for a significant differential in the drive current when the drive motor 527 is in the stall and drive conditions.

FIGS. 10(a) and (b) illustrate a detection apparatus in accordance with a tenth embodiment of the present invention for detecting the location of the tip of a tubular element, in particular a needle, within a region, in particular the epidural space and the peritoneal cavity, of a body of a subject.

The apparatus comprises an elongate tubular element 605, in this embodiment a needle, here embodied as a Touhy needle, an elongate sensing element 607 which extends through the tubular element 605, and a biasing unit 609 for biasing the sensing element 607 with a predetermined biasing force such that the tip of the sensing element 607 is biased outwardly of the tip of the tubular element 605.

In this embodiment the sensing element 607 comprises a plastic element having a blunt tip, but could be a metal element having a blunt tip or a metal element fitted with a blunt plastic tip.

The biasing unit 609 comprises a first body 611 to which the tubular element 605 is attached, in this embodiment at the rearward end thereof, a second body 615 to which the sensing element 607 is attached, in this embodiment at the rearward end thereof, and a biasing element 617 which couples the first and second bodies 611, 615 and biases the sensing element 607 relative to the tubular element 605 such that the tip of the sensing element 607 is biased outwardly of the tip of the tubular element 605. Through providing a constant biasing force, the present inventors have identified that the detection apparatus provides for the more reliable detection of expandable body regions.

In this embodiment the biasing element 617 comprises a resilient bellows structure, but can comprise any biasing means capable of providing a predetermined biasing force, such as a spring element, a magnetic drive, an electromagnetic drive, a pneumatic drive or a motorized drive.

With this configuration, the biasing element 617 maintains a predetermined biasing force on the sensing element 607 such that, when the resistance at the tip of the tubular element 605 is greater than the biasing force, such as when the tip of the tubular element 605 is located in body tissue which provides a relatively high resistance to the movement of the sensing element 607, the sensing element 607 remains stationary relative to the tubular element 605, but, when the resistance at the tip of the tubular element 605 is less than the biasing force, such as when the tip of the tubular element 605 is located in an expandable region in the body of a subject, the tip of the sensing element 607 extends from the tip of the tubular element 605, which extension of the sensing element 607 from the tip of the tubular element 605 is reflected by relative movement of the sensing element 607 and the tubular element 605.

The apparatus further comprises a detection unit 619 for detecting a predetermined movement of the sensing element 607 relative to the tubular element 605.

In this embodiment the detection unit 619 is a capacitance detector and comprises a first capacitance plate 621 of fixed position relative to the tubular element 605, in this embodiment attached to the rear end of the first body 611, a second capacitance plate 623 of fixed position relative to the sensing element 607, in this embodiment attached to the rear end of the sensing element 607, and detection circuitry 625 for detecting a predetermined proximity of the first and second capacitance plates 621, 623 corresponding to a predetermined extension of the tip of the sensing element 607 from the tip of the tubular element 605.

In alternative embodiments the detection unit 619 could be a resistive detector, an inductive detector, an optical detector or a switched detector.

In operation, the tip of the tubular element 605 is inserted into body tissue of a subject. While the distal end of the tubular element 605 is located in body tissue and the resistance as experienced by the blunt tip of the sensing element 607 at the tip of the tubular element 605 is greater than the biasing force of the biasing element 617, the sensing element 607 is disposed within the tubular element 605 against the bias of the biasing force, as illustrated in FIG. 10(b). The tubular element 605 is slowly advanced, typically a millimeter at a time, until such point as the tip of the tubular element 605 enters an expandable region in the body of the subject, in this embodiment the epidural space, at which point the resistance as experienced by the blunt tip of the sensing element 607 at the tip of the tubular element 605 is less than the biasing force of the biasing element 617 and the biasing element 617 acts to extend the tip of the sensing element 607 from the tip of the tubular element 605. This extension of the sensing element 607 from the tip of the tubular element 605 is reflected by relative movement of the tubular element 605 and the sensing element 607, and hence relative movement of the first and second capacitance plates 621, 623 of the detection unit 619. Where the extension of the tip of the sensing element 607 from the tip of the tubular element 605 is greater than a predetermined extent, corresponding to a predetermined proximity of the first and second capacitance plates 621, 623 of the detection unit 619, the detection circuitry 625 signals the location of the tip of the tubular element 605 in an expandable body region. At this point, the sensing element 607 is withdrawn from the tubular element 605 to allow for connection to the tubular element 605.

Finally, it will be understood that the present invention has been described in its preferred embodiments and can be modified in many different ways without departing from the scope of the invention as defined by the appended claims.

For example, in the described embodiments, the delivered detection fluid is a liquid, such as a saline solution, but in other embodiments could be a gas, such as air, or even a mixture of a liquid and a gas.

In ones of the above-described embodiments, fluid is drawn into the fluid chambers 15, 115, 215, 315, 415, 515 at the time of operation, but in alternative embodiments the fluid chambers 15, 115, 215, 315, 415, 515 could be pre-filled.

In ones of the described embodiments, the movable parts are configured to be a sliding fit. For example, ones of the plungers 11, 211, 311, 411, 511 are configured to be a sliding frictional fit in the respective bodies 5, 205, 305, 405, 505 and in a preferred embodiment configured to be a sliding fit with uniform frictional characteristics such as to enable continuous movement of the plungers 11, 211, 311, 411, 511 on the application of a biasing force. Similarly, in the above-described fifth embodiment, the grip member 117 is a sliding frictional fit over the body 105, and in a preferred embodiment configured to be a sliding fit with uniform frictional characteristics such as to enable a smooth, continuous movement of the container 111 in the application of a biasing force to a fluid as contained in the fluid chamber 115. In an alternative embodiment all movable parts could be guided using bearings, typically linear bearings.

In a modification of the above-described ninth embodiment, the drive motor 527 of the biasing unit 525 could be a linear motor which directly drives the plunger 511 of the delivery unit 503.

In addition, the detection apparatuses of the above-described first to eighth embodiments could be modified such as to deliver a predetermined volume of fluid from the fluid outlet 17, 117, 217, 317, 417 into the identified expandable body region. In the above-described seventh and eighth embodiments, the biasing units 325, 425 could be de-actuated at the onset of the loss of resistance at the fluid outlet 317, 417 or following detection of a predetermined movement of the plunger 311, 411 in the manner of the above-described tenth embodiment.

In one embodiment the detection apparatus of the present invention can be employed in a fully-automated system, typically a robotic system, whereby a region in a body of a subject can be located without requiring initial intervention.

The invention claimed is:

1. A detection apparatus configured to position a tip of a tubular element within a region of a body of a subject, the detection apparatus comprising:
a syringe comprising a housing, the housing defining a cavity including a fluid chamber and configured to be coupled to a tubular element, the syringe further comprising a plunger partially contained within the housing and partially external to the housing, the plunger comprising a distal gasket seal that provides a fluid-tight seal with the housing; and
a biasing unit operable to maintain a substantially constant biasing force on a volume of fluid contained in the fluid chamber, the biasing unit comprising a biasing element,
wherein the volume of fluid within the fluid chamber is distal to the biasing element, the fluid chamber being defined by the cavity and the plunger, and
wherein the plunger is configured to be proximally withdrawn and to thereby compress the biasing element, wherein proximal withdrawal of the plunger results in proximal withdrawal of the distal gasket seal, and wherein the syringe delivers the fluid from the tubular element when the biasing force is greater than a resistance to flow of the fluid from the tip of the tubular element.

2. The apparatus of claim 1, wherein the biasing unit is operable to continuously maintain the biasing force on the fluid contained in the housing of the syringe.

3. The apparatus of claim 1, wherein the biasing element normally applies the biasing force on the fluid contained in the syringe.

4. The apparatus of claim 1, wherein the biasing element comprises a resilient element.

5. The apparatus of claim 4, wherein the resilient element comprises a spring element.

6. The apparatus of claim 1, wherein the biasing unit is an electromagnetic unit.

7. The apparatus of claim 1, wherein the biasing unit is a magnetic unit.

8. The apparatus of claim 1, wherein the biasing unit is a pneumatic unit.

9. The apparatus of claim 1, wherein the biasing unit is a motorized unit.

10. The apparatus of claim 9, wherein the motorized unit comprises a drive motor coupled to the delivery unit, and drive circuitry operable to drive the drive motor at a predetermined maximum torque corresponding to the biasing force.

11. The apparatus of claim 1, wherein the biasing unit comprises a body coupled to the housing of the syringe and a drive member movable relative to the body, and wherein the drive member applies the biasing force to the volume of fluid in the housing of the syringe.

12. The apparatus of claim 11, wherein the drive member is coupled to the housing of the syringe such as to enable fluid to be drawn into the housing.

13. The apparatus of claim 1, wherein the housing of the syringe defines a cavity including a fluid chamber, wherein fluid is deliverable through the opening in the housing, and wherein the plunger is movably disposed in the cavity such that fluid can be drawn into the fluid chamber by withdrawing the plunger and expelled from the fluid chamber by depressing the plunger.

14. The apparatus of claim 13, wherein the housing of the syringe includes a variable-volume container disposed in the cavity, the variable-volume container defining the fluid chamber.

15. The apparatus of claim 1, wherein the plunger comprises a shaft defining an elongate cavity therein configured to house a needle element of a needle unit for use with the apparatus.

16. The apparatus of claim 15, further comprising a needle unit comprising a needle element and a connector element attached to the needle element, wherein the connector element is configured to connect the needle element to the shaft of the plunger such that the needle element is housed in the elongate cavity in the shaft of the plunger.

17. The apparatus of claim 1, wherein the plunger comprises a delivery channel configured to allow for the delivery of a substance through the plunger to the opening in the housing of the syringe, and a valve unit configured to provide only one-way delivery of a substance through the delivery channel to the opening in the housing of the syringe.

18. The apparatus of claim 1, wherein the biasing element comprises a resilient, flexible element for normally applying the biasing force on the fluid contained in the housing of the syringe.

19. The apparatus of claim 18, wherein the biasing element comprises a bellows structure.

20. The apparatus of claim 19, wherein the bellows structure is tubular.

21. The apparatus of claim 1, wherein the biasing unit comprises a flexible structure and the biasing element for normally applying the biasing force on the fluid contained in the housing of the syringe.

22. The apparatus of claim 1, wherein the housing of the syringe defines a cavity for containing fluid.

23. The apparatus of claim 1, wherein the delivery unit is separable from the biasing unit.

24. The apparatus of claim 1, wherein the biasing unit and the delivery unit comprise an integral unit.

25. The apparatus of claim 1, wherein the biasing force is such as to maintain the fluid at a pressure not greater than about 8.5 $lbin^{-2}$.

26. The apparatus of claim 25, wherein the biasing force is such as to maintain the fluid at a pressure of from about 0.5 $lbin^{-2}$ to about 8.5 $lbin^{-2}$.

27. The apparatus of claim 26, wherein the biasing force is such as to maintain the fluid at a pressure of from about 0.5 lbin$^{-2}$ to about 5.66 lbin$^{-2}$.

28. The apparatus of claim 27, wherein the biasing force is such as to maintain the fluid at a pressure of from about 2.0 lbin$^{-2}$ to about 5.66 lbin$^{-2}$.

29. The apparatus of claim 28, wherein the biasing force is such as to maintain the fluid at a pressure of from about 2.0 lbin$^{-2}$ to about 3.5 lbin$^{-2}$.

30. The apparatus of claim 1, wherein the housing of the syringe comprises a fluid chamber of variable volume.

31. The apparatus of claim 1, wherein the housing of the syringe is pre-filled with a predetermined volume of fluid.

32. The apparatus of claim 1, wherein the apparatus is configured to provide for the delivery of at least 1 ml of fluid.

33. The apparatus of claim 1, wherein the apparatus is configured to position a tip of a needle within a region of a body of a subject.

34. The apparatus of claim 1, wherein the apparatus is configured to position a tip of a tubular element within an epidural space of a body of a subject.

35. The apparatus of claim 1, wherein the apparatus is configured to position a tip of a tubular element within a peritoneal cavity of a body of a subject.

36. The apparatus of claim 1, wherein the fluid comprises a gas.

37. The apparatus of claim 1, wherein the fluid comprises air.

38. The apparatus of claim 1, wherein the syringe comprises a loss-of-resistance syringe.

39. A detection apparatus configured to position a tip of a tubular element within a region of a body of a subject, the detection apparatus comprising:

a syringe comprising a housing, the housing defining a cavity including a fluid chamber and configured to contain a volume of fluid and to connect to a tubular element, and a plunger partially contained within the housing and partially external to the housing, the plunger comprising a distal gasket seal that provides a fluid-tight seal with the housing; and a spring element operable to maintain a biasing force on the volume of fluid within the fluid chamber, the fluid chamber being distal to the spring element and being defined by the cavity and the plunger, such as to cause the syringe to deliver the fluid from the tubular element when the biasing force is greater than a resistance to flow of the fluid from the tip of the tubular element, wherein the plunger is configured to be proximally withdrawn and to thereby compress the spring element, and wherein proximal withdrawal of the plunger results in proximal withdrawal of the distal gasket seal.

40. The apparatus of claim 39, wherein the apparatus is configured to position a tip of a needle within a region of a body of a subject.

41. The apparatus of claim 39, wherein the apparatus is configured to position a tip of a tubular element within an epidural space of a body of a subject.

42. The apparatus of claim 39, wherein the apparatus is configured to position a tip of a tubular element within a peritoneal cavity of a body of a subject.

43. The apparatus of claim 39, wherein the fluid comprises a gas.

44. The apparatus of claim 39, wherein the fluid comprises air.

* * * * *